United States Patent
Iwasaki et al.

(10) Patent No.: US 8,721,533 B2
(45) Date of Patent: May 13, 2014

(54) IMAGE PICKUP APPARATUS

(71) Applicant: Olympus Medical Systems Corp., Tokyo (JP)

(72) Inventors: Seiji Iwasaki, Hachioji (JP); Hiroshi Ishii, Tokyo (JP); Tomohisa Takahashi, Hachioji (JP); Hiroaki Kagawa, Sagamihara (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 13/731,208

(22) Filed: Dec. 31, 2012

(65) Prior Publication Data
US 2013/0137924 A1 May 30, 2013

Related U.S. Application Data

(62) Division of application No. 12/212,337, filed on Sep. 17, 2008, now Pat. No. 8,366,609.

(30) Foreign Application Priority Data

Sep. 18, 2007 (JP) .................................. 2007-241489
Sep. 27, 2007 (JP) .................................. 2007-252430

(51) Int. Cl.
*A61B 1/06* (2006.01)

(52) U.S. Cl.
USPC ............ 600/181; 600/180; 600/167; 600/168

(58) Field of Classification Search
USPC ................. 600/181, 118, 112, 167, 109, 160; 359/503
See application file for complete search history.

(56) References Cited

U.S. PATENT DOCUMENTS

| 4,777,524 | A | * | 10/1988 | Nakajima et al. | ............. 348/76 |
| 4,860,040 | A | | 8/1989 | Tamamura et al. | |
| 5,056,902 | A | * | 10/1991 | Chinnock et al. | ............ 359/503 |
| 5,150,702 | A | * | 9/1992 | Miyanaga et al. | ........... 600/181 |
| 5,179,934 | A | * | 1/1993 | Nagayoshi et al. | .......... 600/152 |
| 5,609,563 | A | * | 3/1997 | Suzuki et al. | ................. 600/118 |
| 5,876,327 | A | * | 3/1999 | Tsuyuki et al. | ............... 600/112 |
| 6,030,339 | A | * | 2/2000 | Tatsuno et al. | ............... 600/112 |
| 6,080,101 | A | * | 6/2000 | Tatsuno et al. | ............... 600/112 |
| 6,307,678 | B2 | | 10/2001 | Kosaka et al. | |
| 6,327,101 | B1 | * | 12/2001 | Miyano | ........................ 359/691 |

(Continued)

FOREIGN PATENT DOCUMENTS

| JP | 2004-129950 | 4/2004 |
| JP | 2005-003867 | 1/2005 |

(Continued)

*Primary Examiner* — Philip R Smith
*Assistant Examiner* — William Chou
(74) *Attorney, Agent, or Firm* — Scully, Scott, Murphy & Presser, P.C.

(57) ABSTRACT

An actuator has a magnet moved together with a moving lens frame, an SMA wire capable of extending and contracting in a moving direction I of the moving lens frame with execution or non-execution of energization thereof, a fixing member made of a magnetic material attached to a distal end of the SMA wire, a pressing spring which urges the fixing member toward the magnet along the moving direction I, and a stopper member and a stopper portion which limits the movement of the magnet along the moving direction I at a first position or a second position.

8 Claims, 23 Drawing Sheets

(56) References Cited

U.S. PATENT DOCUMENTS

| | | |
|---|---|---|
| 6,949,999 B2 | 9/2005 | Noji |
| 7,125,378 B2 * | 10/2006 | Shimizu et al. ............... 600/112 |
| 7,294,102 B2 | 11/2007 | Jones et al. |
| 7,295,389 B2 | 11/2007 | Ohtsuka et al. |
| 7,448,411 B2 | 11/2008 | Friedman et al. |
| 8,033,994 B2 * | 10/2011 | Purwanto ..................... 600/167 |
| 2003/0103279 A1 * | 6/2003 | Anhalt ........................ 359/826 |
| 2004/0171912 A1 * | 9/2004 | Shimizu ....................... 600/112 |
| 2004/0263299 A1 | 12/2004 | Noji |
| 2005/0143624 A1 | 6/2005 | Iddan |
| 2006/0226713 A1 * | 10/2006 | Lehr et al. ..................... 310/12 |
| 2007/0100209 A1 | 5/2007 | Takahashi |
| 2007/0219409 A1 * | 9/2007 | Shimizu et al. ............... 600/112 |
| 2008/0039696 A1 * | 2/2008 | Kamihara ..................... 600/181 |
| 2008/0272869 A1 * | 11/2008 | Takayama et al. ............. 335/219 |
| 2009/0216081 A1 | 8/2009 | Suzuki et al. |
| 2010/0280316 A1 | 11/2010 | Dietz et al. |
| 2011/0179790 A1 | 7/2011 | Pretorius |

FOREIGN PATENT DOCUMENTS

| | | |
|---|---|---|
| JP | 2005-227705 | 8/2005 |
| JP | 2006-276798 | 10/2006 |
| JP | 2007-229155 | 9/2007 |

* cited by examiner

IMAGE PICKUP APPARATUS

This application is a divisional application of U.S. application Ser. No. 12/212,337 filed on Sep. 17, 2008 which claims the benefit of Japanese Application No. 2007-241489 filed in Japan on Sep. 18, 2007 and Japanese Application No. 2007-252430 filed in Japan on Sep. 27, 2007, the contents of each of which are incorporated by this reference.

BACKGROUND OF THE INVENTION

1. Field of the Invention

The present invention relates to an actuator configured to move a moving portion with expansion/contraction of a shape memory alloy and to an image pickup apparatus used in a medical apparatus such as an endoscope and capable of changing optical performance by the actuator.

2. Description of Related Art

In recent years, endoscopes are widely used in the medical and industrial fields. Endoscopes have an elongated insertion portion inserted in a tube to enable observation in the tube.

An image pickup apparatus including an objective optical system formed of a plurality of objective lens groups for observing the interior of a tube, and a solid-image pickup device or the like such as a CCD is generally provided in a distal end portion at a distal end side in the insertion direction in an insertion portion of an endoscope, e.g., an electronic endoscope, which is configured to pick up an image of an observed portion in a tube formed by the objective optical system.

A zoom endoscope is well known in which at least one lens in a plurality of objective lens groups in an objective optical system is provided as a moving lens capable of moving in an optical axis direction of the objective optical system, and in which optical characteristics including the depth of focus of the objective optical system on an observed portion, the observation magnification and the angle of view can be changed by moving the moving lens in the optical axis direction. By observation using the zoom endoscope in a case where the zoom endoscope is, for example, an endoscope for medical use, mucous membranes, the structure of capillaries, etc., at an observed position in a body cavity can be observed.

Various mechanisms have been proposed as a mechanism for moving in an optical axis direction a moving lens provided as a moving member as described above. For example, Japanese Patent Application Laid-Open Publication No. 2004-129950 discloses a technique to move a moving lens in an optical axis direction by extending and contracting in the optical axis direction a shape memory alloy (hereinafter referred to as SMA) wire extending in the optical axis direction and having its one end fixed to a projection formed integrally on a moving lens frame in which the moving lens is provided. To extend or contract the SMA wire, the SMA wire is set in an energized state or in a non-energized state. That is, the publication discloses a technique to move a moving lens in an optical axis direction by using an actuator having an SMA wire.

Japanese Patent Application Laid-Open Publication No. 2005-003867 discloses a technique to move a moving lens in an optical axis direction by using repellency between a north pole of a drive magnet and a north pole of a follower magnet or repellency between a south pole of the drive magnet and a south pole of the follower magnet. The follower magnet is provided along an optical axis direction on a moving magnet holder fixed on a moving lens barrel holding a moving lens. The drive magnet is held on a drive magnet holder movable in a clockwise direction and in a counterclockwise direction. The drive magnet holder is provided on the outer peripheral side of the moving lens in a diametric direction of the moving lens than the driven magnet. That is, the publication discloses a technique to move a moving lens in an optical axis direction by using an actuator having a follower magnet and a drive magnet.

Other techniques to move a lens moving member in an optical axis direction by magnetic action have been disclosed. For example, Japanese Patent Application Laid-Open Publication No. 2005-227705 discloses one for a lens drive apparatus. Further, Japanese Patent Application Laid-Open Publication No. 2006-276798 discloses a technique to open and close a shutter and a diaphragm by magnetic action in an image pickup apparatus.

Among configurations including a lens movable by changing the optical focal position, the lens drive apparatus described in Japanese Patent Application Laid-Open Publication No. 2005-227705 or the image pickup apparatus described in Japanese Patent Application Laid-Open Publication No. 2006-276798 is provided with a variable diaphragm for adjusting the optimum brightness, i.e., the amount of light in the optical system.

SUMMARY OF THE INVENTION

An actuator according to the present invention has a magnet moved together with a moving portion, a shape memory alloy wire capable of extending and contracting in a direction of movement of the moving portion with execution or non-execution of energization thereof, a fixing member made of a magnetic material attached to a distal end of the shape memory alloy wire, a spring which urges the fixing member toward the magnet along the direction of movement, and a stopper portion which limits the movement of the magnet along the direction of movement at a set position.

A first image pickup apparatus according to the present invention includes an actuator having a magnet moved together with a moving portion, a shape memory alloy wire capable of extending and contracting in a direction of movement of the moving portion with execution or non-execution of energization thereof, a fixing member attached to a distal end of the shape memory alloy wire, a spring which urges the fixing member toward the magnet along the direction of movement, and a stopper portion which limits the movement of the magnet along the direction of movement at a set position. In the first image pickup apparatus, the moving portion is a movable lens frame holding a movable lens, and provided in a movable lens unit having magnetic member, and a fixed lens frame in which a plurality of objective optical systems are disposed, and in which the movable lens frame is held so as to be able to advance and retract in a shooting optical axis direction is provided, and the actuator which advances and retracts the magnetic member of the movable lens frame by magnetic force from the outside of the fixed lens frame.

A second image pickup apparatus according to the present invention has a movable lens unit having a movable lens frame holding a movable lens, and a magnetic member, a fixed lens frame in which a plurality of objective optical systems are disposed, and in which the movable lens frame is held so as to be able to advance and retract in a shooting optical axis direction, a diaphragm unit which adjusts the amount of shooting light by moving a diaphragm blade formed of a magnetic material, and a magnet which moves the diaphragm blade by magnetic force according to the advancement and retraction of the movable lens frame.

The above and other objects, features and advantages of the invention will become more clearly understood from the following description referring to the accompanying drawings.

DETAILED DESCRIPTION OF PREFERRED EMBODIMENTS

Embodiments of the present invention will be described with reference to the drawings. In the embodiments described below, an actuator is described as one used in an endoscope.
(First Embodiment)

Figure 1:
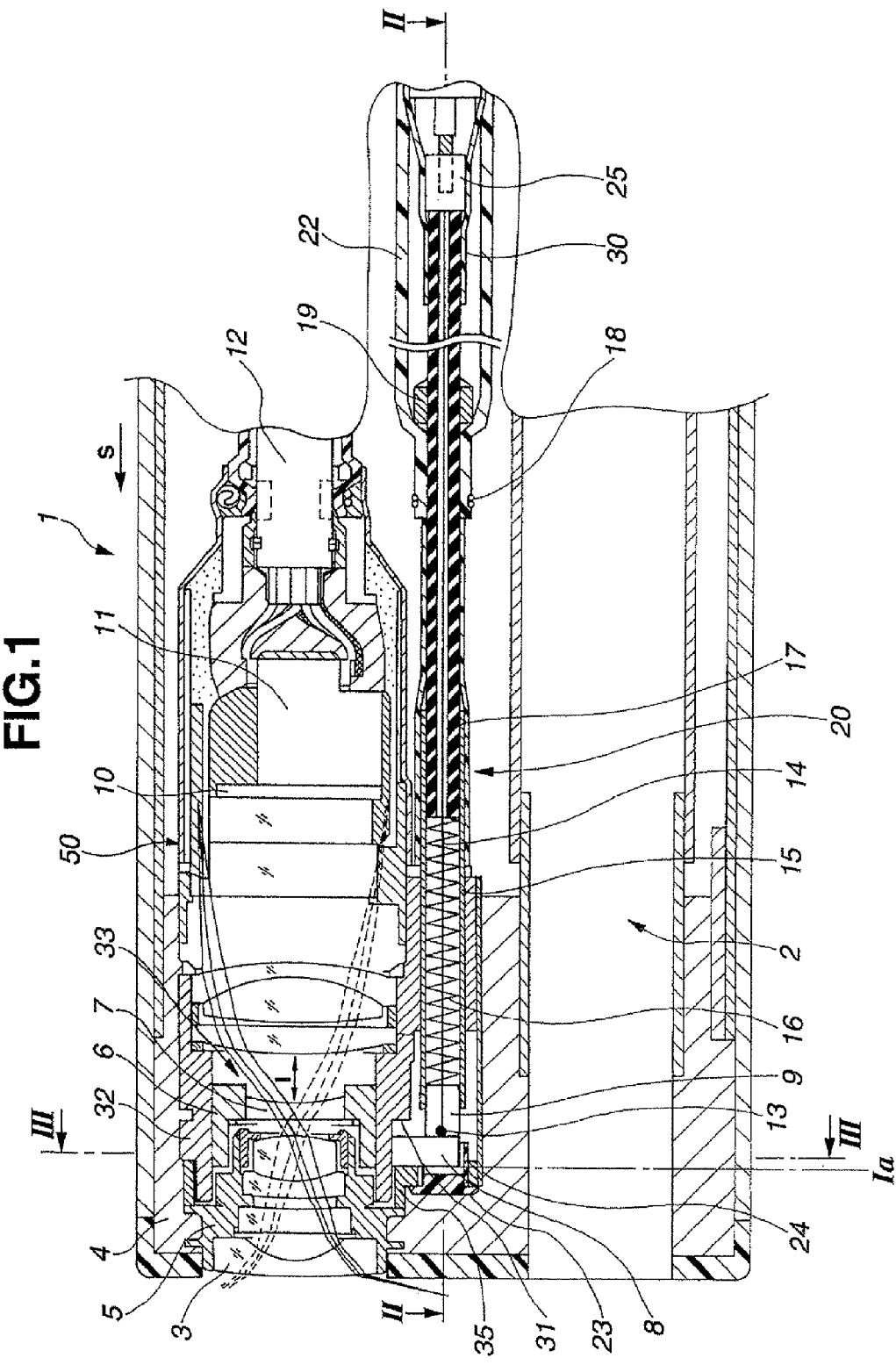
FIG. 1 is a partial sectional view of a distal end portion of an endoscope having an actuator representing a first embodiment.
Figure 2:
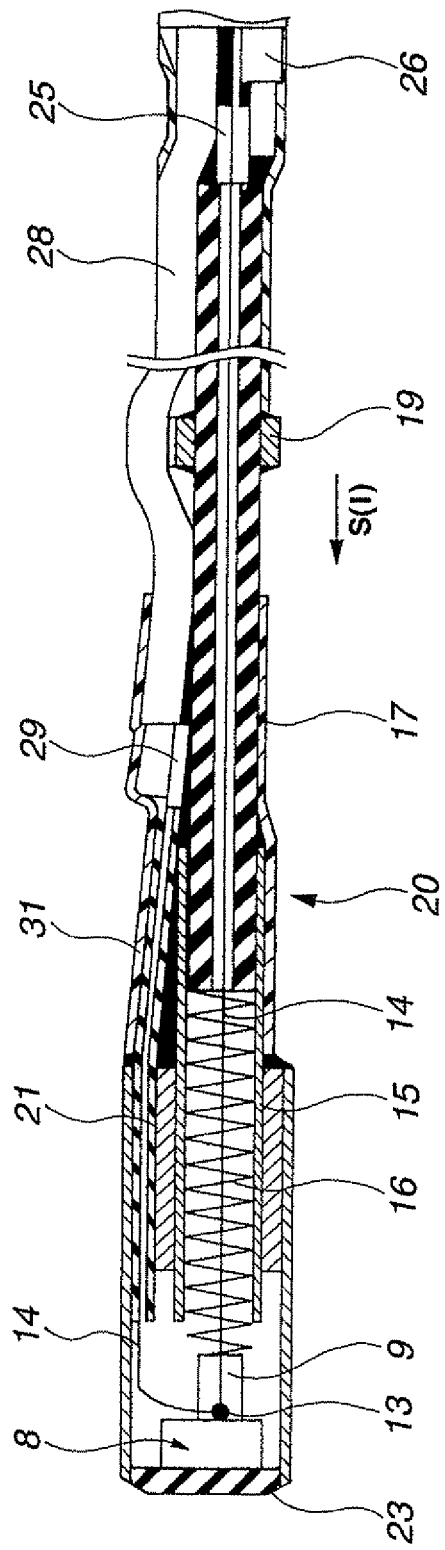
FIG. 2 is a partial sectional view of a distal end portion of the endoscope taken along line II-II in FIG. 1.

FIG. 1 is a partial sectional view of a distal end portion of an endoscope having an actuator according to the present embodiment; FIG. 2 is a partial sectional view of a distal end portion of the endoscope taken along line II-II in FIG. 1; and FIG. 3 is a partial sectional view of a distal end portion of the endoscope taken along line III-III of FIG. 1.

As shown in FIG. 1, a substantially cylindrical distal end holder 4 is provided in a distal end portion 1 of the endoscope along an insertion direction S of the endoscope, and a plurality of through holes are formed in the distal end holder 4 along an insertion direction S.

Figure 3:
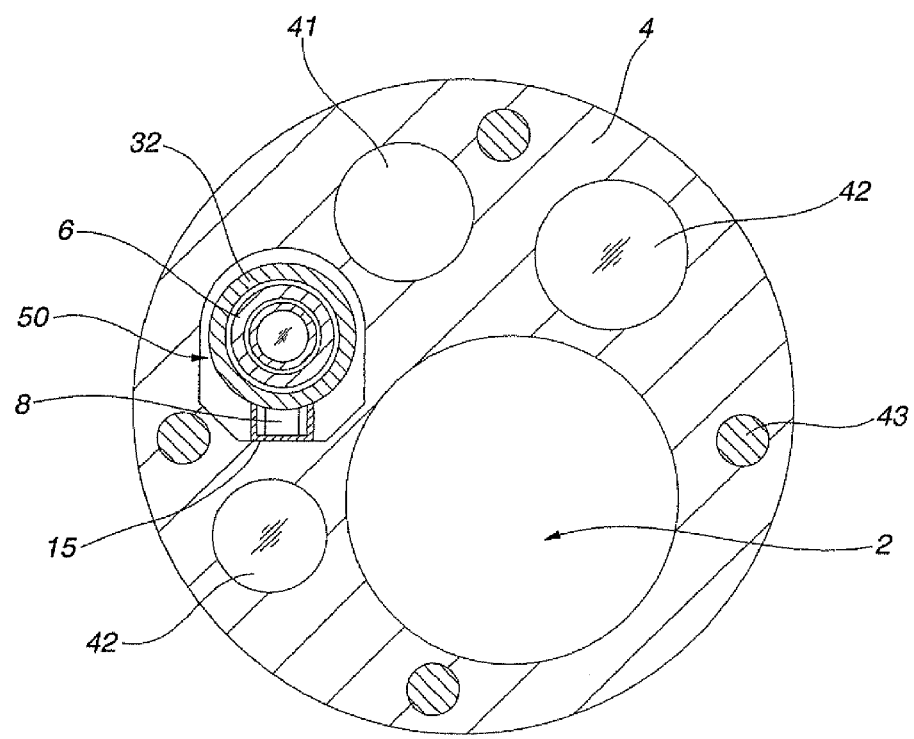
FIG. 3 is a partial sectional view of a distal end portion of the endoscope taken along line III-III of FIG. 1.

As shown in FIG. 3, a channel 2 for insertion of a treatment instrument, which is also used as a suction tube channel, a cleaning nozzle 41 for cleaning an objective lens by jetting a fluid to the lens, an illumination optical system 42 for illuminating a subject portion, which comprises two illumination optical systems in the present embodiment, angling wires 43, an image pickup apparatus 50, or the like are respectively provided in the plurality of through holes formed in the distal end holder 4. The channel 2, the cleaning nozzle 41, the illumination optical systems 42 and the angling wire 43 have well-known configurations and functions, which, therefore, will not be described in the present embodiment.

A configuration of the image pickup apparatus 50 provided in the through hole in the distal end holder 4 will next be described. The image pickup apparatus 50 has a well-known configuration, which therefore will only be outlined.

In the image pickup apparatus 50, a second lens frame 32, which is a nonmagnetic member constituted of a nonmagnetic material, is fitted around an outer periphery of a first lens frame 5 holding an objective lens group 3 constituted of a plurality of objective lenses at an intermediate position on the first lens frame 5 along an insertion direction S.

A stopper member 35, which defines a position to which a magnet 8 described below is moved toward the distal end side in the insertion direction S is fitted around an outer periphery of the second lens frame 32 at a distal end side of the same in the insertion direction S. That is, the stopper member 35 defines a position to which a moving lens frame 6 described below, more particularly a moving lens 7 is moved toward the distal end side in a moving direction I. More specifically, the moving lens 7 is defined to a position corresponding to a 1×1 magnification.

Further, the moving lens frame 6, which is a moving portion holding the moving lens 7, is provided on an inner periphery of the second lens frame 32 so as to be movable in the moving direction I along the insertion direction S in an enclosed space 33 in the second lens frame 32.

In the image pickup apparatus 50, a known solid-state image pickup element 10, an electronic circuit board 11, a signal cable 12 and other components are further provided at the rear of the moving lens 7 in the insertion direction S. A stopper portion 31 formed of a stepped portion is formed in an outer periphery of the second lens frame 32 at an intermediate position in the insertion direction S at the lower side as viewed in FIG. 1.

The stopper portion 31 defies a position to which the magnet 8 is moved toward a rear end side in the insertion direction S. That is, the stopper portion 31 defines a position to which the moving lens frame 6, more particularly the moving lens 7 is moved toward a rear end side in the moving direction I. More specifically, the moving lens 7 is defined at a position corresponding to the maximum magnification.

In the through hole which is formed in the distal end holder 4 and in which the image pickup apparatus 50 is provided, an actuator 20 is provided together with the image pickup apparatus 50.

As shown in FIG. 2, an essential portion of the actuator 20 is configured, along an outer periphery of the moving lens frame 6 at the lower side as viewed in FIG. 1, of the magnet 8, an SMA wire 14, a fixing member 9, a pressing spring 16, the stopper portion 31 formed in the above-described second lens frame 32, and the stopper member 35, the magnet 8 being provided in the lower portion of FIG. 1, via the second lens frame 32.

The magnet 8, the SMA wire 14, the fixing member 9, the pressing spring 16, the stopper portion 31 and the stopper member 35 are disposed by being arranged in a straight line along the moving direction I, as shown in FIG. 1.

The magnet 8 moves by magnetic force in the moving direction I together with the moving lens frame 6. The SMA wire 14 extends and contracts in the moving direction I of the moving lens frame 6 with energization/non-energization of the SMA wire 14. More specifically, the SMA wire 14 is a wire constituted of SMA, having a diameter of several ten micros, contracting in the moving direction I when heated, and extending in the moving direction I when cooled.

The SMA wire 14 is inserted in a guide pipe 15 and in a first insulating tube 17 provided along the insertion direction S. The first insulating tube 17 is fixed by being fitted at its distal end side in an inner periphery of the guide pipe 15 at the proximal end side in the insertion direction S.

One end of the SMA wire 14 is swaged in a first swaged portion 25 formed of a cylindrical metal ring. A drive cable 26 through which a current is supplied to the SMA wire is electrically connected to the first swaged portion 25 by soldering. The connection between the first swaged portion 25 and the drive cable 26 is reinforced on the periphery thereof by an adhesive or the like, not shown in the figure.

The position in which the first swaged portion 25 is mounted is set at a position on the distal end side in the insertion direction S of a flexible tube portion not shown in the figure, provided continuously with a bending portion of the endoscope on the proximal end side.

The SMA wire 14 is inserted at an intermediate position in a groove formed in the fixing member 9 but not shown in the figure and is bent so as to be turned back along the insertion direction S. The portion of the SMA wire 14 inserted in the groove in the fixing member 9 is bonded and fixed to the fixing member 9 by a ball 13.

The other end of the SMA wire 14 turned back is swaged in a second swaged portion 29 formed of a cylindrical metal ring. A GND cable 28 is electrically connected to the second waged portion 29 by soldering.

An anchor 19 in ring form is fitted around portions of outer peripheries of the first insulating tube 17 and the GND cable 28 (the anchor 19 provided on the portion of the outer periphery of the GND cable 28 is not shown in FIG. 2) and are bonded and fixed to the portions of the outer peripheries.

A protective tube 22 is attached to the first insulating tube 17 and the GND cable 28 so as to cover the anchor 19 and the first insulating tube 17, as shown in FIG. 1. The protective tube 22 is fixed at its distal end in the insertion direction S to the first insulating tube 17 by binding with a string 18 such as an artificial silkworm gut.

The fixing member 9 is attached to the distal end of the SMA wire 14 in the moving direction I and is constituted of a magnetic material.

The pressing spring 16 is provided between the first insulating tube 17 and the fixing member 9 in the guide pipe 15. The pressing spring 16 urges the fixing member 9 toward the magnet 8 along the moving direction I, so that the fixing member 9 constituted of a magnetic material can be attracted and attached to the magnet 8 by magnetic force.

Figure 4:
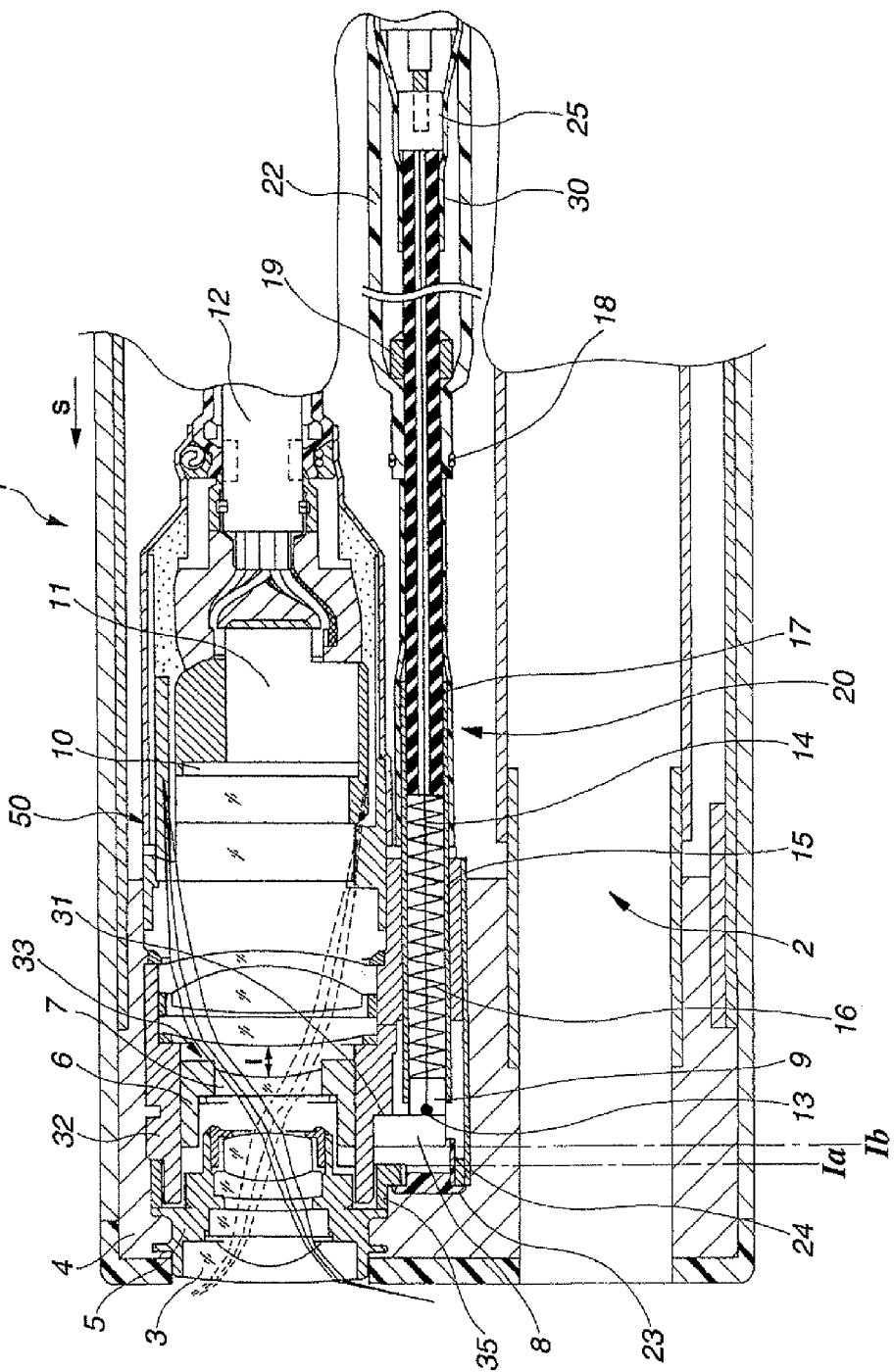
FIG. 4 is a partial sectional view of a distal end portion of the endoscope, showing a state in which a magnet shown in FIG. 1 is brought into abutment on a stopper portion of a second lens frame.
Figure 5:
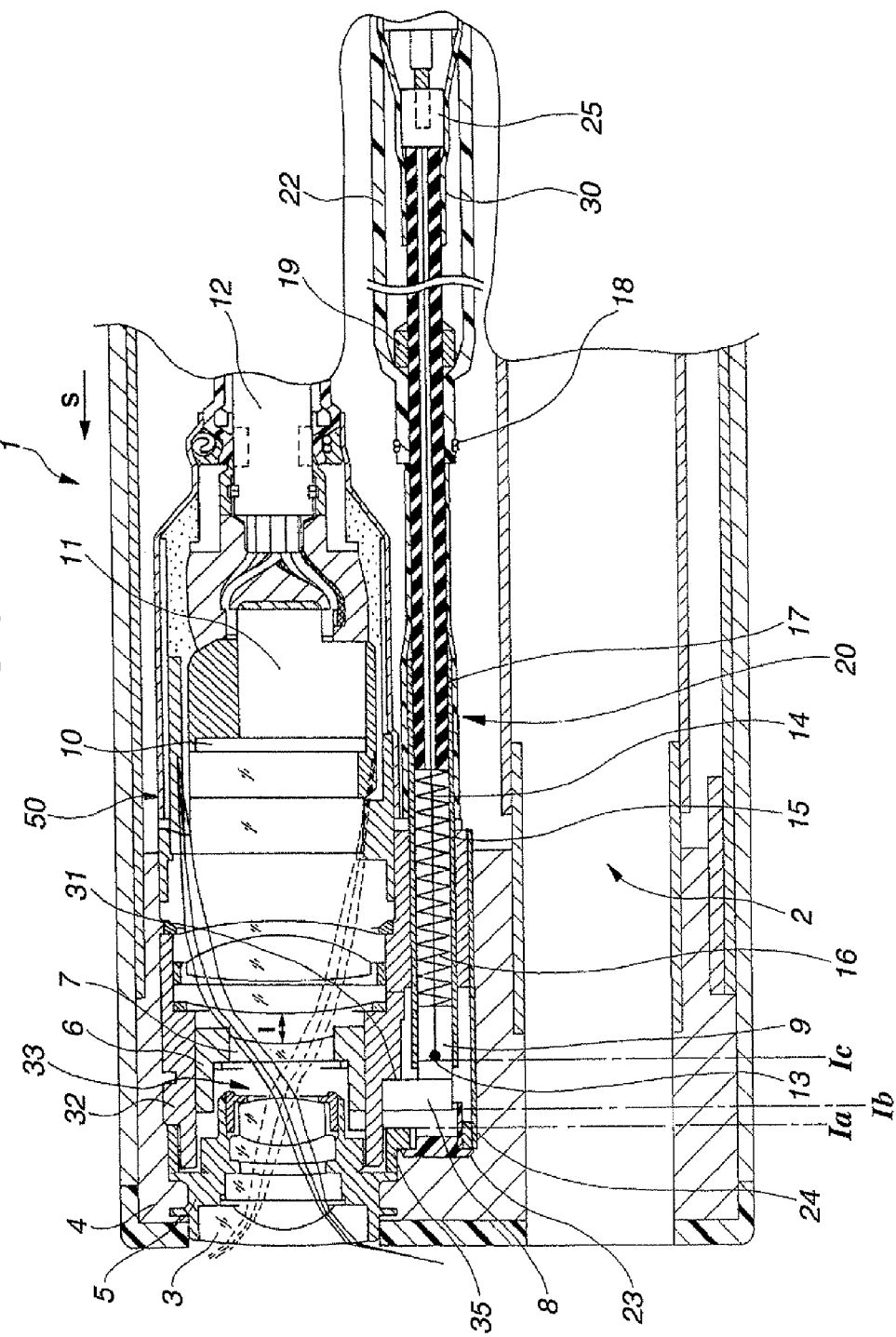
FIG. 5 is a partial sectional view of the distal end portion of the endoscope, showing a state in which a fixing member is moved apart from the magnet when the magnet shown in FIG. 4 is in abutment on the stopper portion of the second lens frame.
Figure 6:
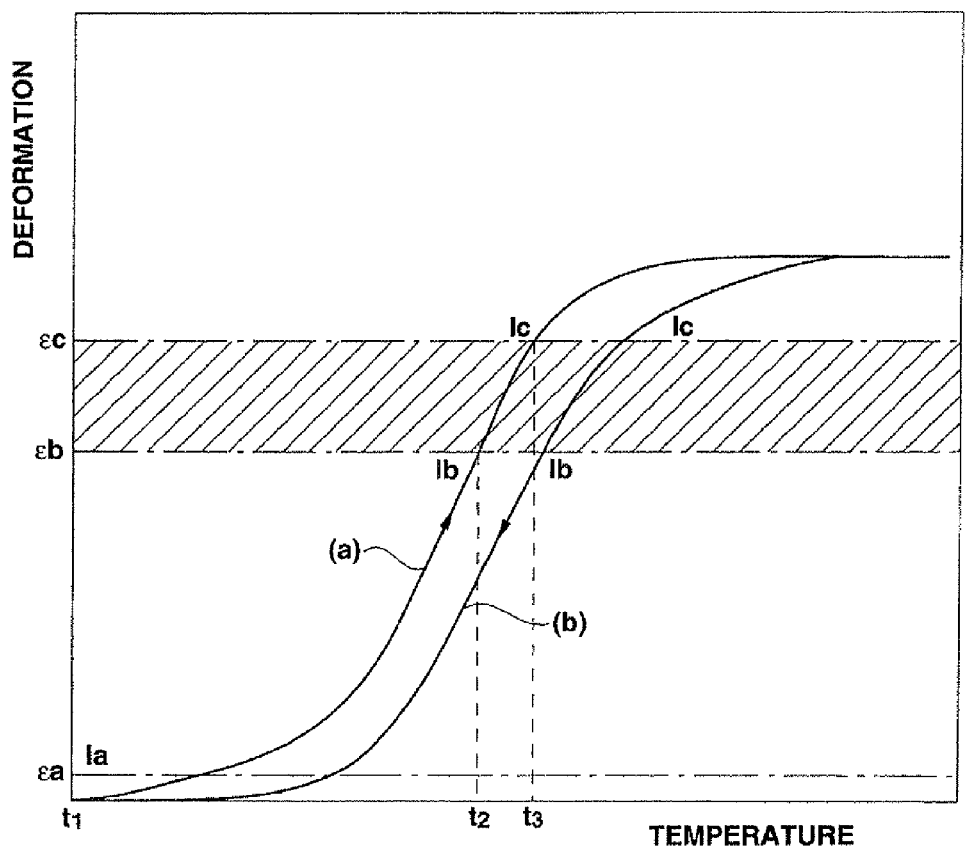
FIG. 6 is a graph showing, as a hysteresis curve, changes in the amount of deformation with respect to the temperature of an SMA wire shown in FIG. 1.

The operation of the present embodiment thus configured will be described with reference to FIGS. 4 to 6 as well as to FIGS. 1 to 3 described above. FIG. 4 is a partial sectional view of a distal end portion of the endoscope showing a state in which the magnet shown in FIG. 1 is brought into abutment on the stopper portion of the second lens frame. FIG. 5 is a partial sectional view of the distal end portion of the endoscope showing a state in which the fixing member is moved apart from the magnet when the magnet in FIG. 4 is in abutment on the stopper portion of the second lens frame. FIG. 6 is a graph showing, as a hysteresis curve, changes in the amount of distortion with respect to the temperature of the SMA wire shown in FIG. 1.

First, when the moving lens 7 is moved to a first position Ia which is a set position corresponding to 1×1 magnification, the SMA wire 14 of the actuator 20 is set in a non-energized state. As a result, the SMA wire 14 extends toward the distal end side in the moving direction I, and the fixing member 9 is pressed by the pressing spring 16 toward the distal end side in the moving direction I to press the magnet 8 against the stopper member 35 in a state of being attached to the magnet 8 by magnetic force, as shown in FIG. 1. As a result, the moving positions of the moving lens frame 6 and the moving lens 7 are fixed at the distal-most end side of the moving direction I, i.e., the first position Ia corresponding to 1×1 magnification in the moving range from Ia to Ib. The amount of deformation of the SMA wire 14 at this time is represented by ea and the temperature at this time is represented by t1. Also, at this time, the magnet 8 and the stopper portion 31 are separate from each other.

Next, when the moving lens 7 is moved to a second position Ib corresponding to the maximum magnification, that is, the moving lens 7 is moved to the rear end side in the moving direction I, a current is supplied from a power supply not shown in the figure to the drive cable 26 in the actuator 20.

Thereafter, the current flows through the drive cable 26, the first swaged portion 25, the SMA wire 14, the second swaged portion 29 and the GND cable 28, and the SMA wire 14 produces heat and contracts so that the amount of deformation changes from εa to εb with respect to the temperature of the SMA wire 14 from t1 to t2, as indicated by a curve (a) in FIG. 6.

As a result, the fixing member 9 to which the SMA wire 14 is fixed is moved rearward in the moving direction I and the magnet 8 that has attached to the fixing member 9 by magnetic force is also moved rearward in the moving direction I while attaching to the fixing member 9. Further, the moving lens frame 6 and the moving lens 7 are also moved rearward in the moving direction I in the enclosed space 33 by the magnetic force of the magnet 8.

The magnet 8 is then brought into abutment on the stopper portion 31 of the second lens frame 32, as shown in FIG. 4. The amount of deformation of the SMA wire 14 at this time is represented by εb and the temperature at this time is represented by t2. The stopper portion 31 stops the magnet 8 from moving rearward in the moving direction I from the second position Ib, which is a set position at which it abuts on the stopper portion 31, even when the SMA wire 14 contracts further. That is, the moving lens frame 6 and the moving lens 7 that have been moved rearward in the moving direction I by the magnetic force of the magnet 8 are defined in the rearmost position in the moving range of the moving lens frame 6 and the moving lens 7. In other words, the moving lens 7 is moved to the second position Ib corresponding to the maximum magnification to fix the moving position. At this time, the magnet 8 and the stopper member 35 are separate from each other.

When the SMA wire 14 contracts further so that the amount of deformation with respect to the temperature of the SMA wire 14 from t2 to t3 is εb to εc as indicated by the curve (a) in FIG. 6 in the state where the magnet 8 is in abutment on the stopper portion 31 at the second position Ib, the fixing member 9 is separated from the magnet 8 and moved rearward in the moving direction I to a third position Ic for example, as shown in FIG. 5.

When the fixing member 9 is separated from the magnet 8, the magnet 8 remains in abutment on the stopper portion 31, and the moving lens frame 6 and the moving lens 7 remain at the second position Ib.

Also, when the fixing member 9 is separated from the magnet 8, that is, the SMA wire 14 does not pull the magnet 8 by contraction in the state where the magnet 8 is in abutment on the stopper portion 31, no excessive load is applied to the SMA wire 14.

The reason for the effect of maintaining the magnet 8 in abutment on the stopper portion 31 even when the fixing member 9 is separated from the magnet 8 is that magnetic force acts between the fixing member 9 and the magnet 8 even after the fixing member 9 has been separated from the magnet 8 if the separation distance in the moving direction I is not large, and that the moving lens frame 6 abuts on the inner periphery of the second lens frame 32 with frictional force due to the magnetic force between the magnet 8 and the moving lens frame 6.

It can be understood that if the amount of deformation of the SMA wire 14 at the third position Ic is εc and the temperature of the SMA wire 14 is t3, the amount of deformation (from εb to εc) with respect to a unit temperature (from t2 to t3) in the case of deformation from the second position Ib to the third position Ic after bringing the magnet 8 into abutment on the stopper portion 31 does not differ largely from the amount of deformation (from εa to εb) with respect to the unit temperature from the first position Ia to the second position Ib (from t1 to t2), as indicated by the curve (a) in FIG. 6.

It can also be understood that when the SMA wire 14 contracts beyond the third position Ic, the amount of deformation with respect to the unit temperature is reduced relative to the amount of deformation (from εa to εc) from the first position Ia to the third position Ic is small or is zero, as indicated by the curve (a) in FIG. 6.

That is, in the present embodiment, the SMA wire 14 is contracted in the range from εa to εc in which the amount of deformation of the SMA wire 14 is substantially constant with respect to the unit temperature in the temperature range from t1 to t3 when the fixing member 9 is moved from the first position Ia to the third position Ic, as shown in FIG. 6. In other words, an excessively heated state in which the SMA wire 14 is contracted to such a degree that the amount of deformation is equal to or larger than εc is not reached. It can, therefore, be understood that when energization of the SMA wire 14 is stopped, the amount of deformation is instantly reduced as indicated by the curve (a) in FIG. 6, that is, the SMA wire 14 extends instantly, in comparison with a case where the SMA wire 14 is contracted until an amount of deformation of εc or more is reached.

When energization of the SMA wire 14 is stopped at the third position Ic shown in FIG. 5, the fixing member 9 is moved toward the distal end side in the moving direction I by the pressing spring 16 until it is attached to the magnet 8 at the second position Ib by magnetic force. At this time, the SMA wire 14 extends so that the amount of deformation of the SMA wire 14 changes from εc to εb as indicated by a curve (b) in FIG. 6.

The magnet 8 is further moved toward the distal end side from the second position Ib shown in FIG. 4 by the pressing spring 16 until it is brought into abutment on the stopper member 35 at the first position Ia. At this time, the moving lens frame 6 and the moving lens 7 are also moved in the moving direction I from the second position Ib to the first position Ia. Also, the SMA wire 14 extends so that the amount of deformation of the SMA wire 14 changes from εb to εa, as indicated by the curve (b) in FIG. 6.

The non-coincidence between the curves (a) and (b) with respect to the contraction and the extension of the SMA wire 14 as indicated by the curve (a) and the curve (b) in FIG. 6, i.e., the difference between the amounts of deformation per unit temperature between the contraction and the extraction is due to a known hysteretic phenomenon.

It has been described that, in the actuator 20 in the present embodiment, the magnet 8, the SMA wire 4, the fixing member 9, the pressing spring 16, the stopper portion 31 and the stopper member 35 are disposed by being arranged in a straight line along the moving direction I, and the moving lens 7 and the moving lens frame 6 that are moved in the moving direction I in the enclosed space 33 by the magnetic force of the magnet 8 are positioned at the first position Ia when the magnet 8 is in abutment on the stopper member 35, and are positioned at the second position Ib by the magnetic force of the magnet 8 when the magnet 8 is maintained in abutment on the stopper portion 31 by contraction of the SMA wire 14. It has also been described that when the SMA wire 14 is contracted from the second position Ib, the fixing member 9 is separated from the magnet 8.

According to this arrangement, in which the magnet 8, the SMA wire 4, the fixing member 9, the pressing spring 16, the stopper portion 31 and the stopper member 35 are disposed by being arranged in a straight line along the moving direction I, the actuator 20 is increased in length in the moving direction I but can be reduced in size in comparison with the one in the conventional arrangement because it is not increased in size in a diametric direction.

Also, when the SMA wire 14 is contracted from the second position Ib, the fixing member 9 is separated from the magnet

8 while the magnet 8 is in abutment on the stopper portion 31. In this state, the magnet 8 is not pulled rearward in the moving direction I by the SMA wire 14 with the fixing member 9. In this way, application of an uncontrollable large force to the SMA wire 14 is prevented. As a result, the durability of the SMA wire 14 can be improved.

It has also been described that in the present embodiment the SMA wire 14 is contracted in the temperature range from t1 to t3 in which any excessively heated state is not reached, as described above.

Accordingly, when energization of the SMA wire 14 is stopped to establish a non-energized state after supplying a current to the SMA wire 14 and thereby contracting the SMA wire 14, the SMA wire 14 extends at a constant deformation rate. Therefore, the SMA wire 14 can be caused to extend with an increased response speed. As a result, the response speed of the actuator 20 is improved.

It has also been described that in the present embodiment the moving lens 7 and the moving lens frame 6 are movable in the moving direction I in the enclosed space 33 in the second lens frame 32 by the magnetic force of the magnet 8.

Accordingly, permeation of a fluid into the second lens frame 32 is prevented and the gastightness is improved.

Thus, an actuator can be provided which has a configuration in which a moving lens frame and a moving lens are moved by using an SMA wire and the positions of the moving lens frame and the moving lens are defined by using a stopper portion, and which is capable of preventing a reduction in response speed and a reduction in durability and realizing a reduction in size in a diametric direction of the moving lens frame and the moving lens.

A modified example will be described below.

It has been described that, in the present embodiment, the SMA wire 14 is contracted so that the magnet 8 abuts on the stopper portion 31 when the moving lens frame 6 and the moving lens 7 are moved from the first position Ia to the second position Ib, and the fixing member 9 is thereafter separated from the magnet 8.

However, the present invention is not limited thereto. Contraction of the SMA wire 14 may be controlled by determining a target current value. This target current value is determined by applying a minute voltage when supply of the current to the SMA wire 14 is paused and by detecting the resistance value with a bridge circuit not shown in the figure.

That is, the amount of energization of the SMA wire 14 may be controlled so that the SMA wire 14 is contracted from the extended state at the first position Ia in the non-energized state to the contracted state at the second position Ib in the energized state.

Further, the abutment between the magnet 8 and the stopper portion 31 at the second position Ib (the state of abutment) may be detected, for example, with a sensor such as a short detection circuit provided on the stopper portion 31 and control may be performed on the basis of the detected state so that a predetermined current is supplied to the SMA wire 14. Detection of abutment between the magnet 8 and the stopper portion 31 may be performed by detecting a change in the value of resistance against the current for energization of the SMA wire 14.

If the above-described modified example is used, prevention of application of a load to the SMA wire 14 can be achieved without separating the magnet 8 and the fixing member 9 by contacting the SMA wire 14 from the second position Ib, because supply of the current to the SMA wire 14 is stopped after binging the magnet 8 into abutment on the stopper portion 31.

Figure 12:
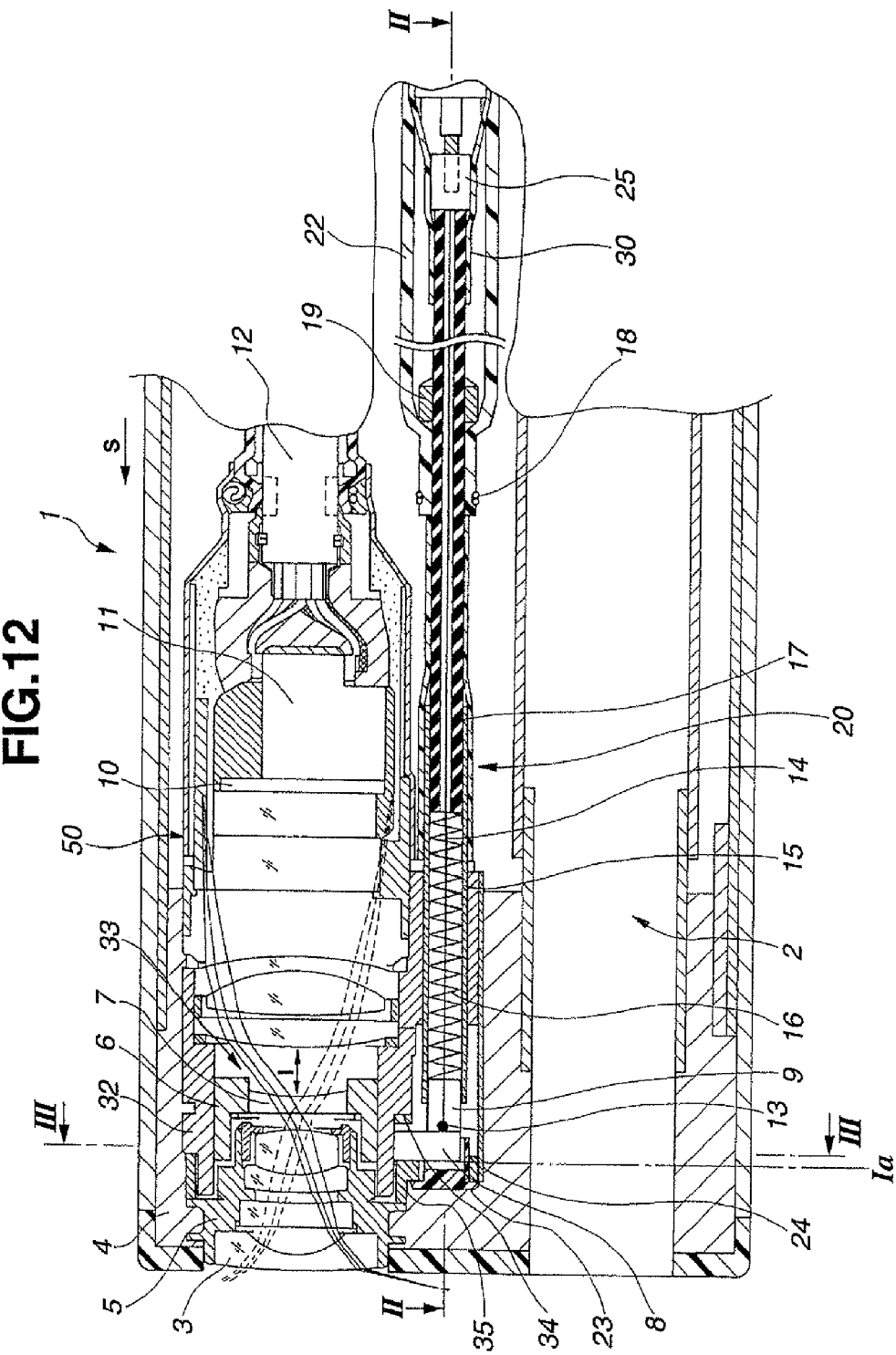
FIG. 12 is a partial sectional view of a distal end portion of an endoscope having an actuator representing a modified example of the present embodiment in which a stopper member is provided on the stopper portion shown in FIG. 1.

Another modified example will be described with reference to FIG. 12. FIG. 12 is a partial sectional view of a distal end portion of an endoscope having an actuator representing a modified example of the present embodiment in which a stopper member is provided on the stopper portion shown in FIG. 1.

As shown in FIG. 12, a stopper member 34 made of a magnetic material may be provided on the stopper portion 31 provided in the second lens frame 32. In the case where the stopper member 34 made of a magnetic material is provided, the magnet 8 and the stopper member 34 attach to each other by the magnetic force of the magnet 8 when the magnet 8 is moving to Ib and, therefore, the magnet 8 remains at the position Ib more reliability in comparison with the above-described first embodiment.

(Second Embodiment)

A second embodiment of the present invention will be described.

Figure 7:
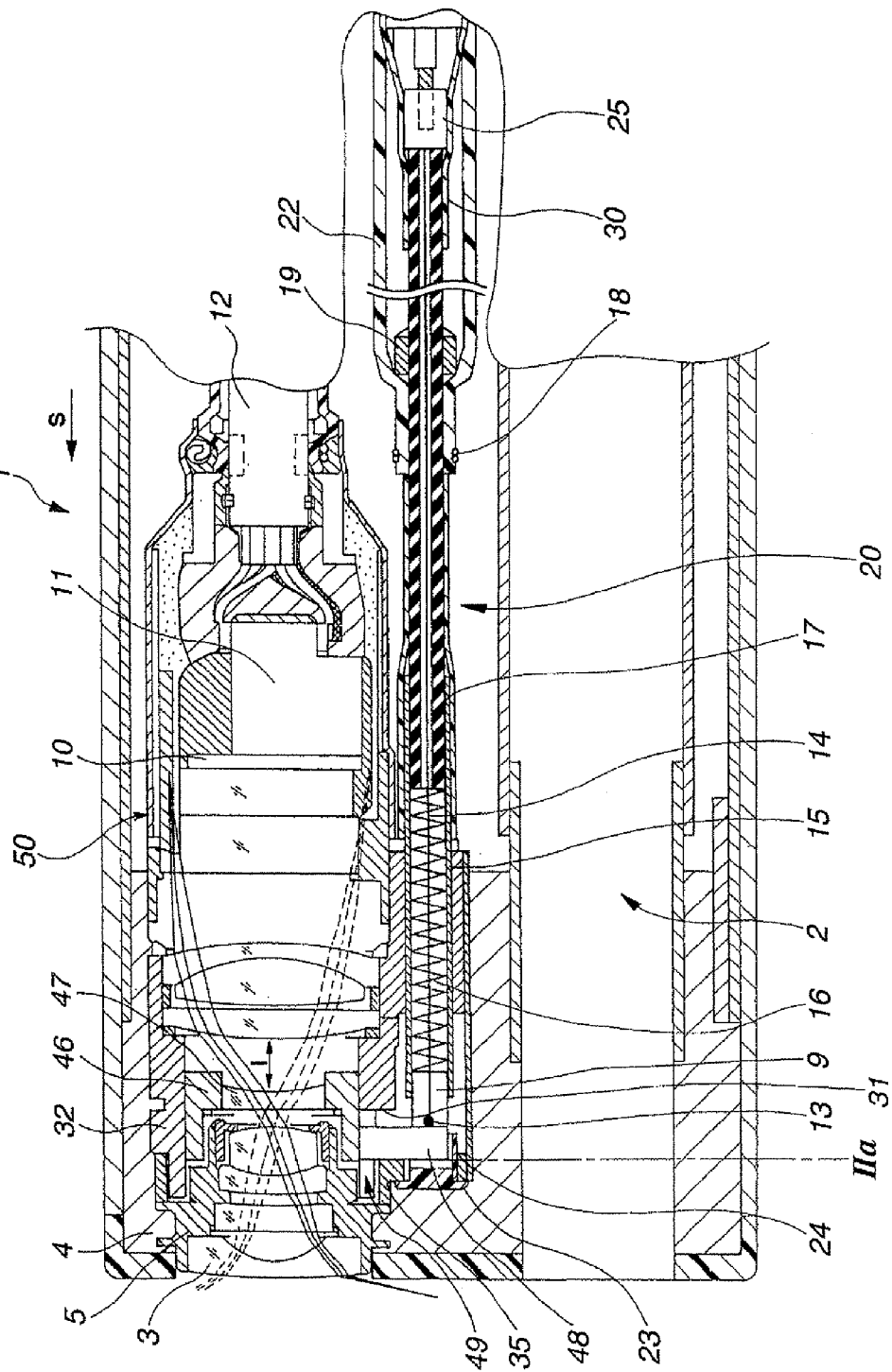
FIG. 7 is a partial sectional view of a distal end portion of an endoscope having an actuator representing a second embodiment.
Figure 8:
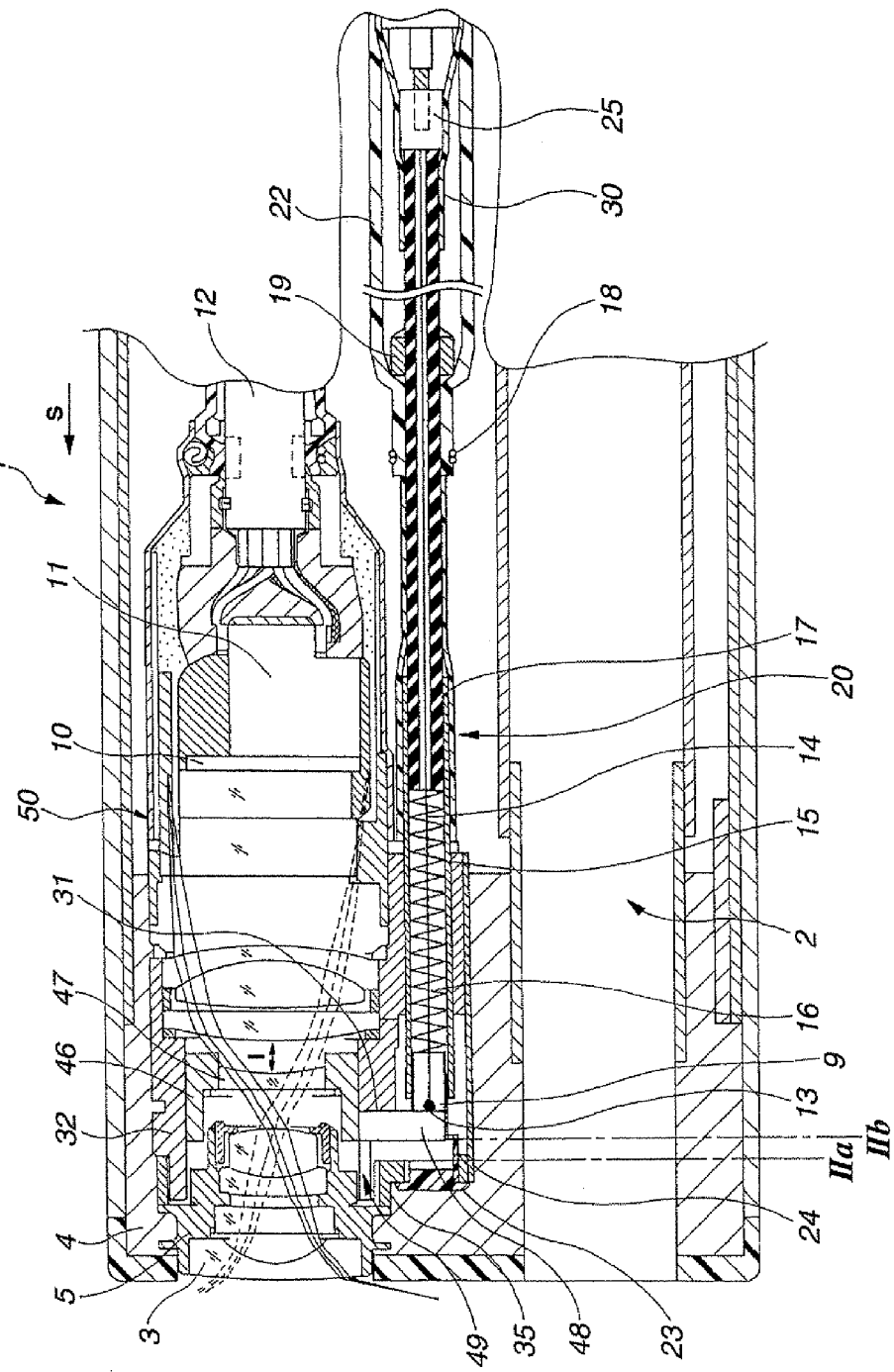
FIG. 8 is a partial sectional view of the distal end portion of the endoscope, showing a state in which a magnet shown in FIG. 7 is brought into abutment on a stopper portion of a second lens frame.
Figure 9:
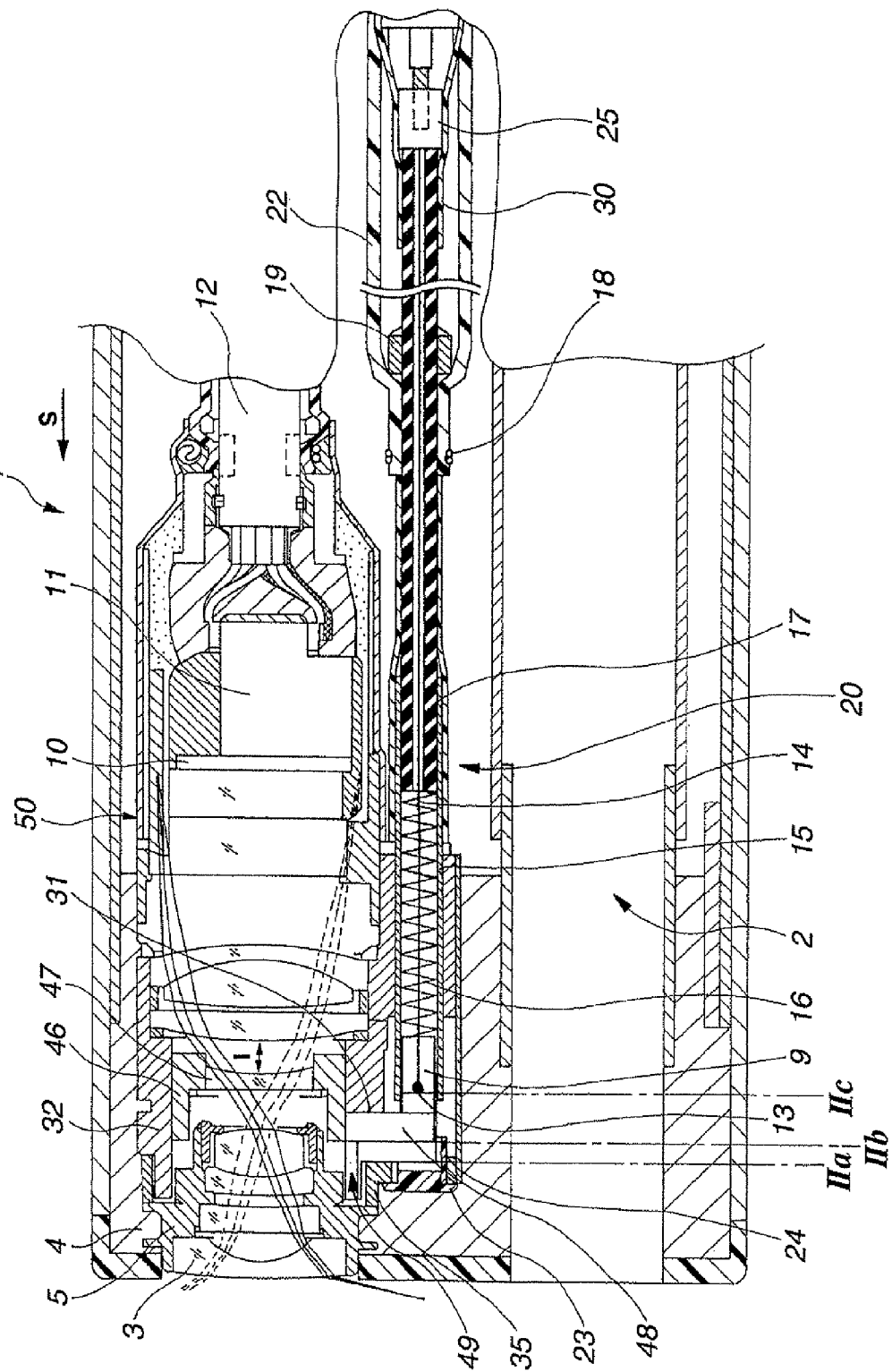
FIG. 9 is a partial sectional view of the distal end portion of the endoscope, showing a state in which a fixing member is moved apart from the magnet when the magnet shown in FIG. 7 is in abutment on the stopper portion of the second lens frame.

FIG. 7 is a partial sectional view of a distal end portion of an endoscope having an actuator representing the present embodiment; FIG. 8 is a partial sectional view of the distal end portion of the endoscope, showing a state where a magnet shown in FIG. 7 is brought into abutment on a stopper portion of a second lens frame; and FIG. 9 is a partial sectional view of the distal end portion of the endoscope, showing a state where the magnet shown in FIG. 7 is in abutment on the stopper portion of the second lens frame, and where a fixing member is moved apart from the magnet.

The configuration of the actuator in the second embodiment differs from that of the above-described actuator in the first embodiment shown in FIGS. 1 to 6 in that a magnet directly attaches to a moving lens frame by magnetic force. Description will be made only of this point of difference. The same components in the configuration as those in the first embodiment are indicated by the same reference numerals, and the description thereof will not be repeated.

In the present embodiment, as shown in FIG. 7, a moving lens 47 is held by a moving lens frame 46 which is a moving portion constituted of a magnetic material, and the moving lens frame 46 is provided so as to be movable in the moving direction I in the second lens frame 32.

A cut 49 is formed in the second lens frame 32 along the moving direction I at the lower side of the second lens frame 32 as viewed in FIG. 7, and a connecting rod magnet 48 in the actuator 20 is directly attached to the moving lens frame 46 through the cut 49 by magnetic force. In other respects, the configuration is the same as that of the above-described first embodiment.

The operation of the present embodiment thus configured will next be described.

First, when the moving lens 7 is moved to a first position IIa which is a set position corresponding to 1×1 magnification, the SMA wire 14 of the actuator 20 is set in a non-energized state. As a result, the SMA wire 14 extends toward the distal end side in the moving direction I, and the fixing member 9 is pressed by the pressing spring 16 toward the distal end side in the moving direction I to press the connecting rod magnet 48 against the stopper member 35 in a state of being attached to the connecting rod magnet 48 by magnetic force, as shown in FIG. 7. As a result, the moving positions of the moving lens frame 46 and the moving lens 47 are fixed at the distal-most end side, i.e., the first position IIa corresponding to 1×1 magnification in the moving range from IIa to IIb. Also, at this time, the connecting rod magnet 48 and the stopper portion 31 are separate from each other.

Next, when the moving lens 47 is moved to a second position IIb corresponding to the maximum magnification, that is, the moving lens 47 is moved to the rear end side in the moving direction I, a current is supplied from a power supply not shown in the figure to the drive cable 26 in the actuator 20.

Thereafter, the current flows through the drive cable 26, the first swaged portion 25, the SMA wire 14, the second swaged portion 29 and the GND cable 28, and the SMA wire 14 produces heat and contracts.

As a result, the fixing member 9 is moved rearward in the moving direction I and the connecting rod magnet 48 that has attached to the fixing member 9 by magnetic force is moved rearward in the moving direction I through the cut 49 while attaching to the fixing member 9. Further, the moving lens frame 46 and the moving lens 47 are also moved rearward in the moving direction I by the magnetic force of the connecting rod magnet 48 through the cut 49.

The connecting rod magnet 48 is then brought into abutment on the stopper portion 31 of the second lens frame 32, as shown in FIG. 8. The stopper portion 31 stops the connecting rod magnet 48 from moving rearward in the moving direction I from the second position IIb, which is a set position at which the connecting rod magnet 48 abuts on the stopper portion 31, even when the SMA wire 14 contracts. That is, the moving lens frame 46 and the moving lens 47 that have been moved rearward in the moving direction I by the magnetic force of the connecting rod magnet 48 are defined in the rearmost position in the moving range of the moving lens frame 46 and the moving lens 47. In other words, the moving lens 47 is moved to the second position IIb corresponding to the maximum magnification to fix the moving position. At this time, the connecting rod magnet 48 and the stopper member 35 are separate from each other.

When the SMA wire 14 contracts further in the state where the connecting rod magnet 48 is in abutment on the stopper portion 31 at the second position IIb, the fixing member 9 is separated from the connecting rod magnet 48 and moved rearward in the moving direction I to a third position IIc for example, as shown in FIG. 9.

When the fixing member 9 is separated from the connecting rod magnet 48, the connecting rod magnet 48 remains in abutment on the stopper portion 31, and the moving lens frame 46 and the moving lens 47 remain at the second position IIb.

Also, when the fixing member 9 is separated from the connecting rod magnet 48, that is, the SMA wire 14 does not pull the connecting rod magnet 48 by contraction in the state where the connecting rod magnet 48 is in abutment on the stopper portion 31, no excessive load is applied to the SMA wire 14.

When energization of the SMA wire 14 is stopped at the third position IIc shown in FIG. 9, the fixing member 9 is moved toward the distal end side in the moving direction I by the pressing spring 16 until it is attached to the connecting rod magnet 48 at the second position IIb by magnetic force. At this time, the SMA wire 14 extends.

The connecting magnet 48 is further moved toward the distal end side in the moving direction I from the second position IIb shown in FIG. 8 by the pressing spring 16 until it is brought into abutment on the stopper member 35 at the first position IIa through the cut 49. At this time, the moving lens frame 46 and the moving lens 47 are also moved in the moving direction I from the second position IIb to the first position IIa. The SMA wire 14 is further extended. In other respects, the operation is the same as that in the above-described first embodiment.

It has been described that in the present embodiment the connecting rod magnet 48 is directly attached to the moving lens frame 46 by magnetic force through the cut 49. Accordingly, the gastightness on the moving lens frame 46 is reduced as a result of the provision of the cut 49 in comparison with the above-described first embodiment. However, when the moving lens frame 46 moves along the moving direction I, no frictional resistance is produced between the connecting rod magnet 48 and the second lens frame 32 and, therefore, the connecting rod magnet 48 can be moved more smoothly in comparison with the first embodiment. That is, an actuator having improved response speed can be provided. Other effects are the same as those in the above-described first embodiment.

While an example of attachment between the second lens frame 32 and the connecting rod magnet 48 by magnetic force in the second embodiment has been described, the second lens frame 32 and the connecting rod magnet 48 may be fixed to each other with an adhesive. If the second lens frame 32 and the connecting rod magnet 48 are bonded to each other with an adhesive, the magnetic force of the connecting rod magnet 48 does not have to be strong and so the connecting rod magnet 48 may have reduced magnetic force since there is no possibility of disengagement of the second lens frame 32 and the connecting rod magnet 48.

(Third Embodiment)

A third embodiment of the present invention will be described.

Figure 10:
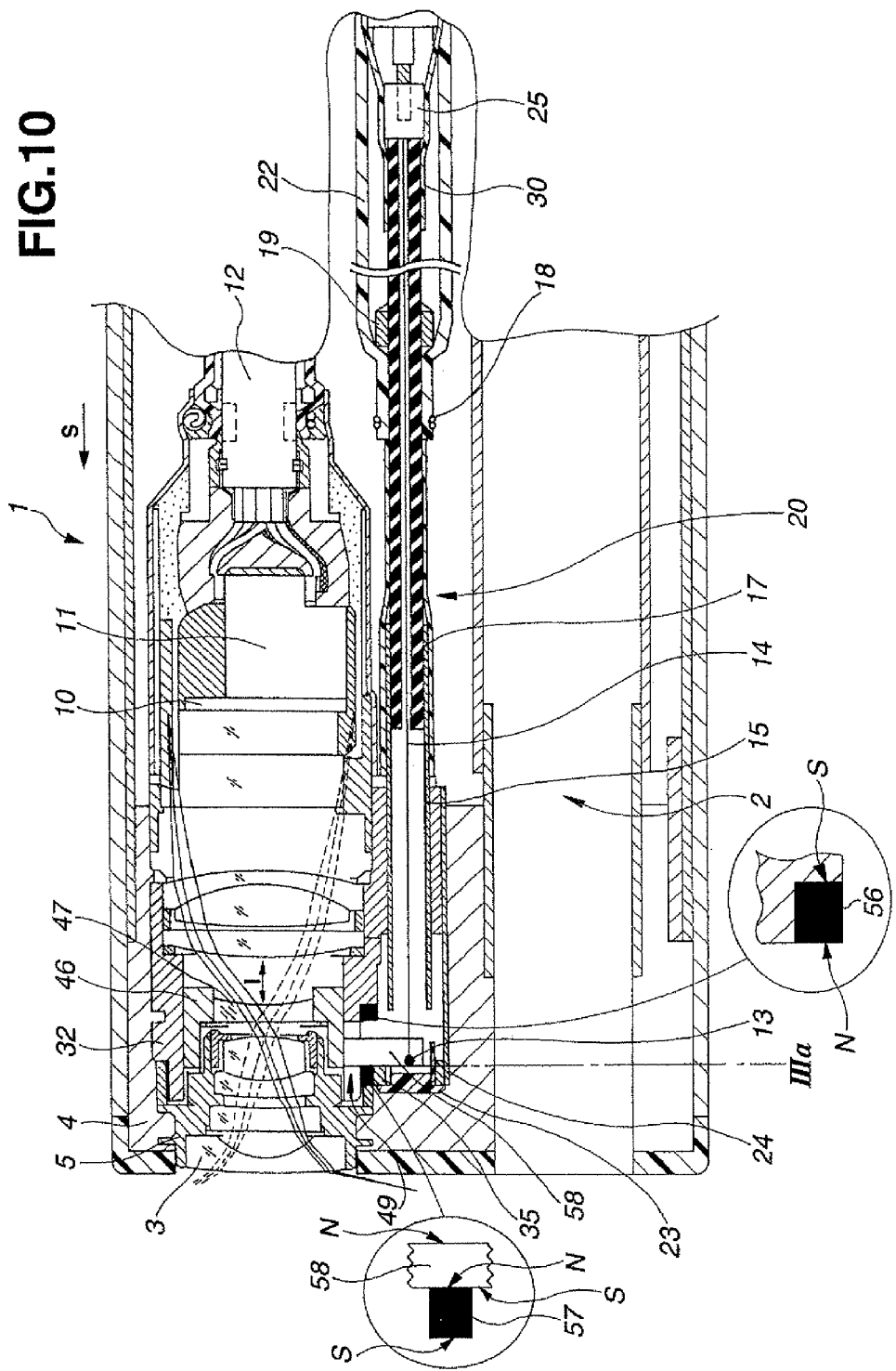
FIG. 10 is a partial sectional view of a distal end portion of an endoscope having an actuator representing a third embodiment.
Figure 11:
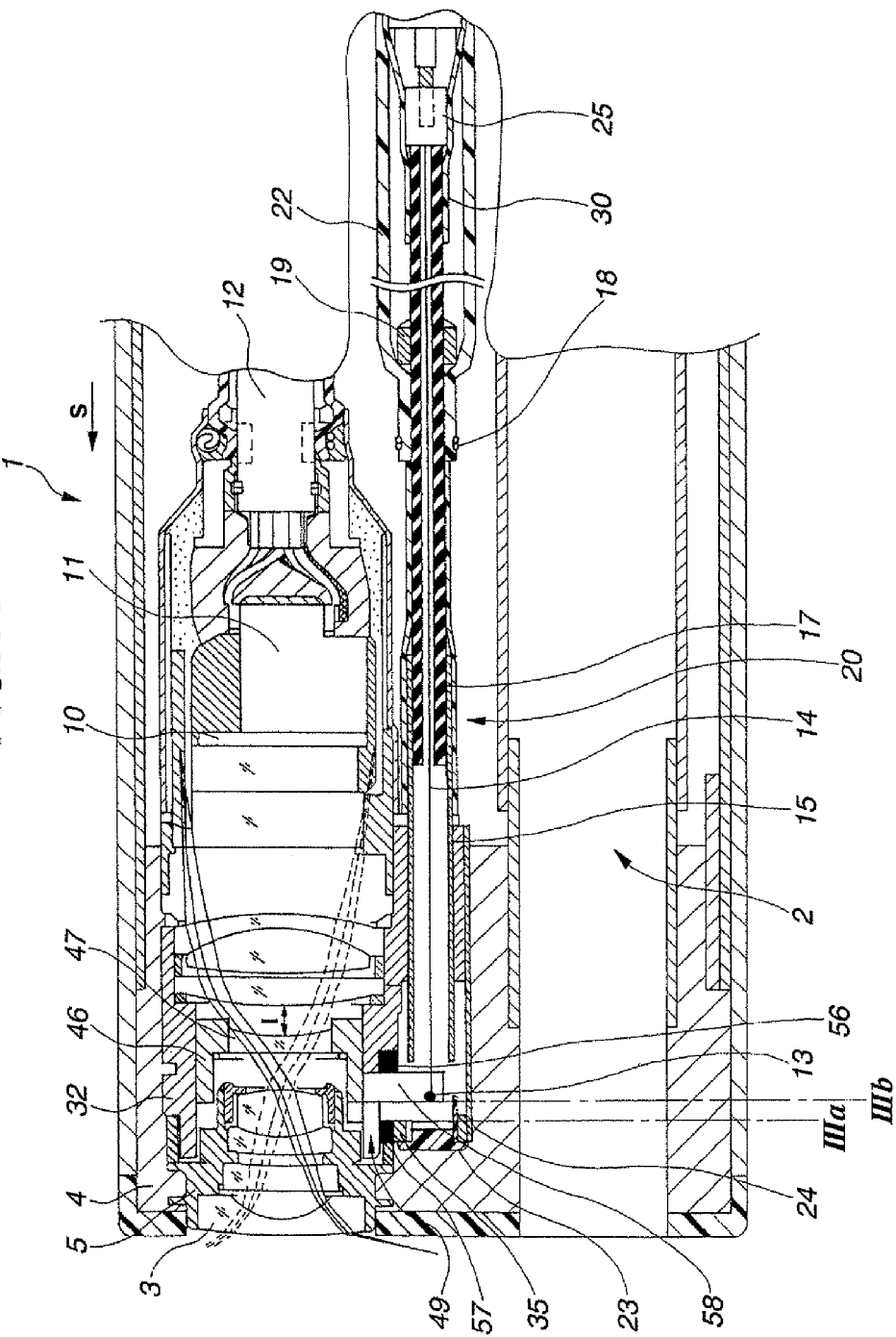
FIG. 11 is a partial sectional view of the distal end portion of the endoscope, showing a state in which a magnet shown in FIG. 10 is attached to a rear magnet in a second lens frame.

FIG. 10 is a partial sectional view of a distal end portion of an endoscope having an actuator representing the present embodiment, and FIG. 11 is a partial sectional view of the distal end portion of the endoscope, showing a state where a magnet shown in FIG. 10 is attached to a rear magnet in a second lens frame.

The configuration of the actuator in the third embodiment differs from that of the above-described actuator in the second embodiment described above with reference to FIGS. 7 to 9 in that a connecting rod magnet is moved in the moving direction between first and second positions by magnetic force. Description will be made only of this point of difference. The same components in the configuration as those in the second embodiment are indicated by the same reference numerals, and the description thereof will not be repeated.

In the present embodiment, as shown in FIG. 10, a cut 49 is formed in the second lens frame 32 along the moving direction I at the lower side of the second lens frame 32 as viewed in FIG. 10, and a connecting rod magnet 58 in the actuator 20 is directly attached to the moving lens frame 46 through the cut 49 by magnetic force.

A front magnet 57 is provided in a portion of the stopper member 35 on which the connecting rod magnet 58 abuts at a first position IIIa. The front magnet 57 is disposed so that the magnetic pole of the front magnet 57 on the connecting rod magnet 58 side and the magnetic pole of the connecting rod magnet 58 on the front magnet 57 side differ in polarity from each other. For example, the north pole of the front magnet 57 and the south pole of the connecting rod magnet 58 are opposed to each other, and the south pole of the front magnet 57 and the north pole of the connecting rod magnet 58 are remote from each other.

Further, a rear magnet 56 is provided in a portion of the second lens frame 32 on which the connecting rod magnet 58 abuts at a second position IIIb. The rear magnet 56 is disposed so that the magnetic pole of the rear magnet 56 on the connecting rod magnet 58 side and the magnetic pole of the connecting rod magnet 58 on the rear magnet 56 side are equal in polarity to each other. For example, the north pole of the rear magnet 56 and the north pole of the connecting rod magnet 58 are opposed to each other, and the south pole of the rear magnet 56 and the south pole of the connecting rod magnet 58 are remote from each other.

The actuator 20 in the present embodiment is configured differently from that in the above-described second embodiment in that the pressing spring and the fixing member are not used. That is, the tip of the SMA wire 14 in the insertion direction S is fixed to the connecting rod magnet 58. In other respects, the configuration is the same as that of the above-described second embodiment.

The operation of the present embodiment thus configured will next be described.

First, when the moving lens 7 is moved to the first position IIIa which is a set position corresponding to 1×1 magnification, the SMA wire 14 of the actuator 20 is set in a non-energized state. As a result, the SMA wire 14 extends toward the distal end side in the moving direction I, and the south pole of the connecting rod magnet 58 and the north pole of the front magnet 57 are attached to each other by magnetic force, as shown in FIG. 10.

As a result, the moving positions of the moving lens frame 46 and the moving lens 47 are fixed at the distal-most end side in the moving direction I, i.e., the first position IIIa corresponding to 1×1 magnification in the moving range from IIIa to IIIb.

Next, when the moving lens 47 is moved to the second position IIIb corresponding to the maximum magnification, that is, the moving lens 47 is moved to the rear end side in the moving direction I, a current is supplied from a power supply not shown in the figure to the drive cable 26 in the actuator 20.

Thereafter, the current flows through the drive cable 26, the first swaged portion 25, the SMA wire 14, the second swaged portion 29 and the GND cable 28, and the SMA wire 14 produces heat and contracts.

As a result, the connecting rod magnet 58 is moved rearward in the moving direction I by the contraction of the SMA wire 14. Further, the moving lens frame 46 and the moving lens 47 are also moved rearward in the moving direction I by the magnetic force of the connecting rod magnet 58.

The connecting rod magnet 58 is then brought into abutment on the rear magnet 56 in the second lens frame 32, as shown in FIG. 11. At this time, since each of the magnetic poles of the connecting rod magnet 58 and the rear magnet 56 is a north pole, these magnets repel each other. However, the contracting force of the SMA wire 14 is larger than the repelling force, so that the connecting rod magnet 58 is brought into abutment of the rear magnet 56 in the second lens frame 32.

Because of the existence of the rear magnet 56, the connecting rod magnet 58 is not moved rearward in the moving direction I from the second position IIIb even if the SMA wire 14 is further contracted. That is, the rearmost positions of the moving lens frame 46 and the moving lens 47 that have moved backward in the moving direction I by the magnetic force of the connecting rod magnet 58 in the moving range are set. In other words, the moving lens 47 is moved to the second position IIIb corresponding to the maximum magnification to fix the moving position.

If in the present embodiment the SMA wire 14 is contracted in the state where the connecting rod magnet 58 is in abutment on the rear magnet 56, there is a possibility of a load being applied to the SMA wire 14. However, if energization amount control is performed on the SMA wire 14 as described above, application of a load to the SMA wire 14 can be prevented.

When energization of the SMA wire 14 is stopped at the second position IIIb shown in FIG. 11, the connecting rod magnet 58 is moved toward the distal end side in the moving direction I by repellency due to equality in polarity (north pole) between the connecting rod magnet 58 and the rear magnet 56 opposed to each other until the connecting rod magnet 58 is attached to the front magnet 57 at the first position IIIa. At this time, the moving lens frame 46 and the moving lens 47 are also moved in the moving direction I from the second position IIIb to the first position IIIa. The SMA wire also extends. In other respects, the operation is the same as that in the above-described second embodiment.

It has been described that in the present embodiment the front magnet 57 having a magnetic pole differing in polarity from a magnetic pole of the connecting rod magnet 58 facing the magnetic pole of the front magnet 57 is disposed in the stopper member 35 on which the connecting rod magnet 58 abuts at the first position IIIa, and the rear magnet 56 having a magnetic pole equal in polarity to a magnetic pole of the connecting rod magnet 58 facing the magnetic pole of the rear magnet 56 is disposed in the second lens frame 32 on which the connecting rod magnet 58 abuts.

According to this arrangement, the front magnet 57 and the rear magnet 56 are disposed in place of the pressing spring in the actuator 20 to enable the actuator 20 to be reduced in a diametric direction by an amount corresponding to the thickness of the pressing spring in the diametric direction. Also, since the structure is simplified, the assembly of the actuator 20 is made easier. Other effects are the same as those in the third embodiment.

In the first to third embodiments, the moving lens frame holding the moving lens has been described by way of example as a moving portion moved in the moving direction I with an actuator. However, the present invention is not limited thereto. Needless to say, any moving portion moved by using an actuator may suffice if moves rectilinearly.

In the first to third embodiments, the actuator has been described with respect to use in an endoscope. However, the present invention is not limited thereto. Needless to say, the actuator may be used in any other thing.

(Fourth Embodiment)

A fourth embodiment of the present invention will be described with reference to the drawings. In the present embodiment, an example of an image pickup apparatus incorporated in a rigid electronic endoscope used in a laparoscopic surgery among endoscopic apparatuses provided as a medical apparatus inserted in a body cavity to observe a living tissue.

An image pickup apparatus according to the fourth embodiment of the present invention will be described with reference to FIGS. 13 to 22.

Figure 13:
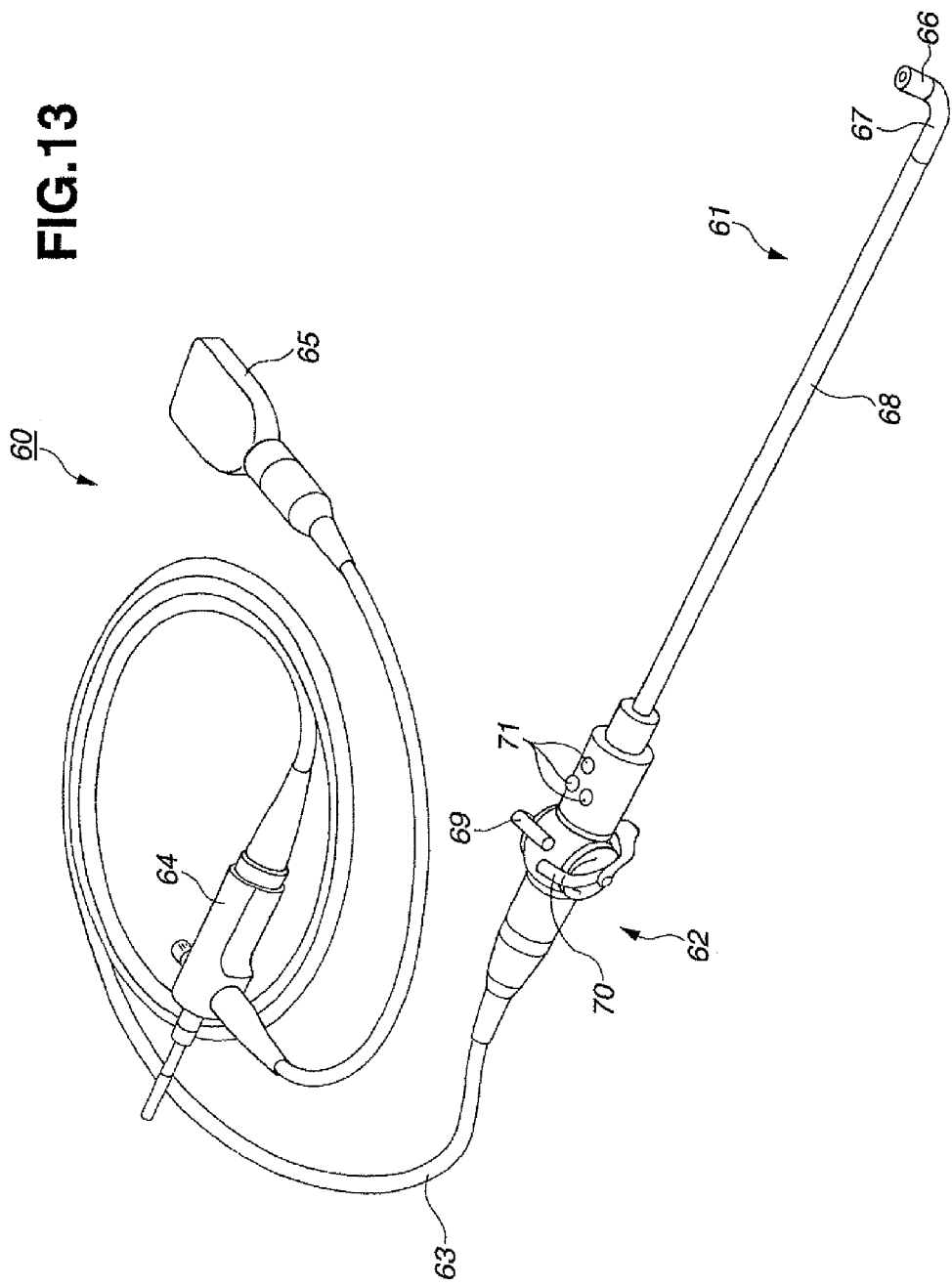
FIG. 13 is a diagram showing a configuration of a rigid electronic endoscope according to a fourth embodiment.
Figure 14:
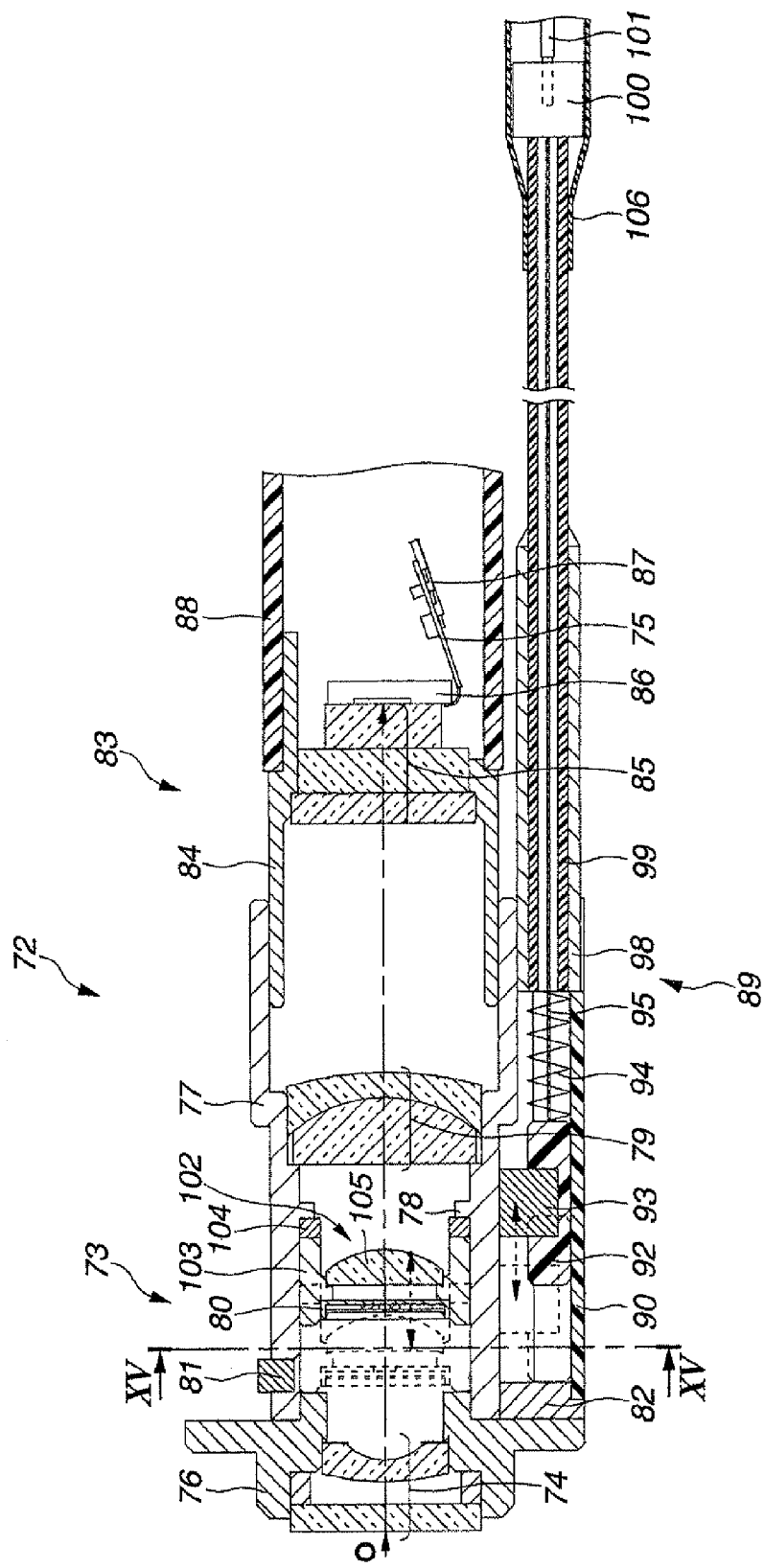
FIG. 14 is a sectional view of an image pickup apparatus disposed in a distal end portion of the rigid electronic endoscope.
Figure 15:
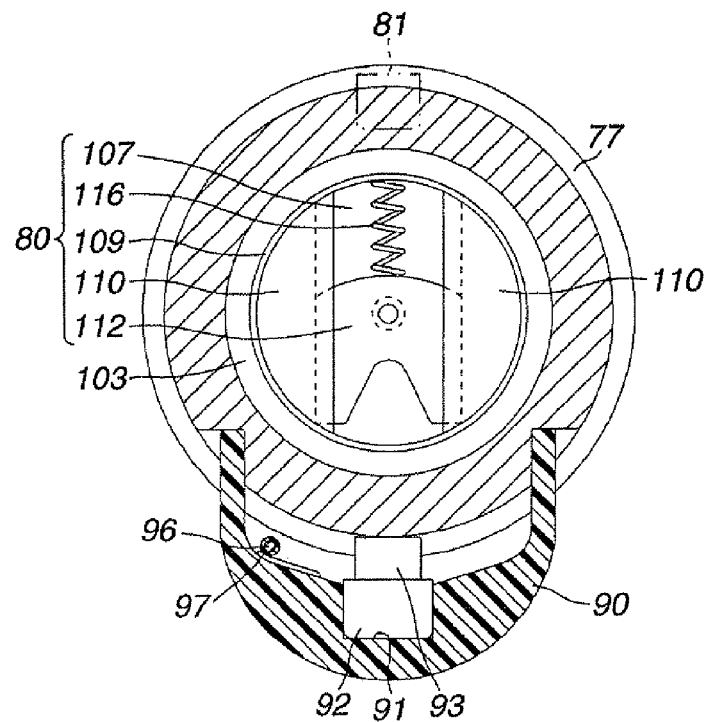
FIG. 15 is a sectional view taken along line XV-XV in FIG. 14.
Figure 16:
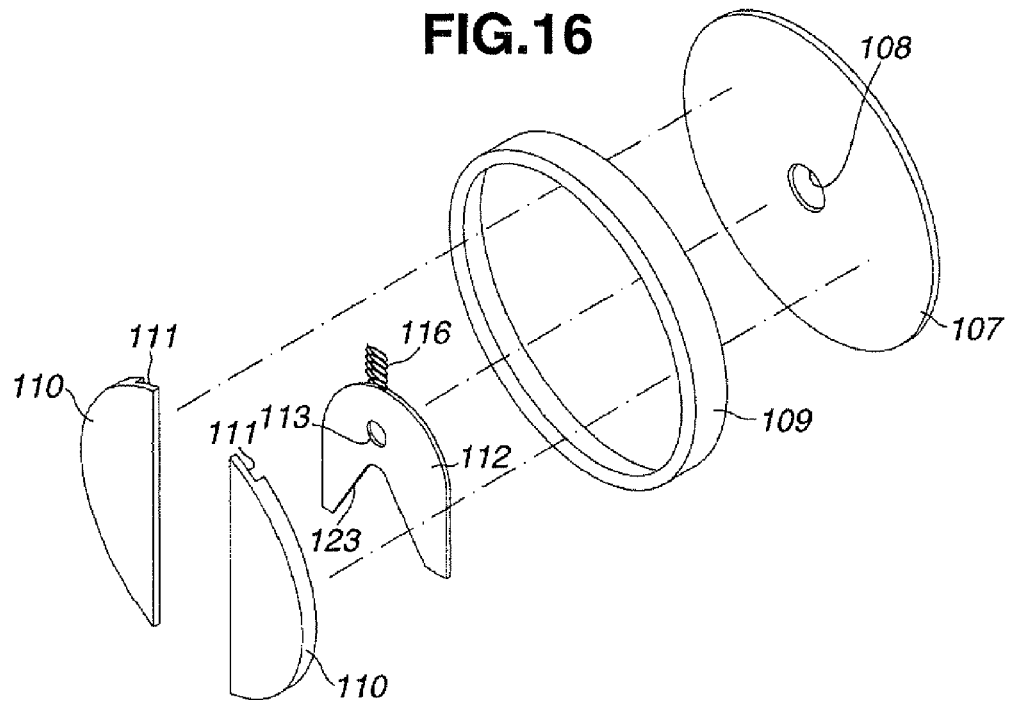
FIG. 16 is an exploded perspective view of a diaphragm unit.
Figure 17:
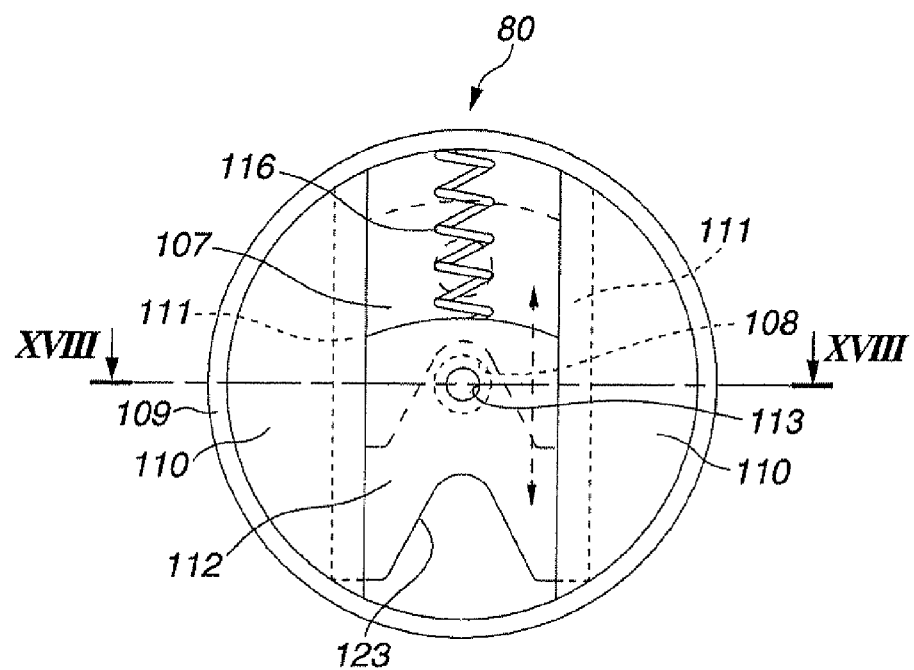
FIG. 17 is a front view of the diaphragm unit.
Figure 18:
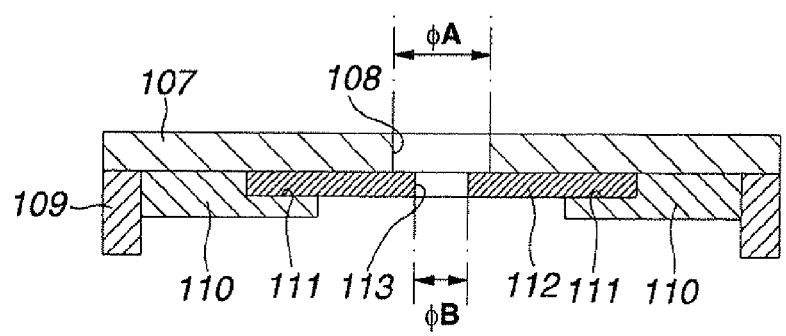
FIG. 18 is a sectional view taken along line XVIII-XVIII in FIG. 17.
Figure 19:
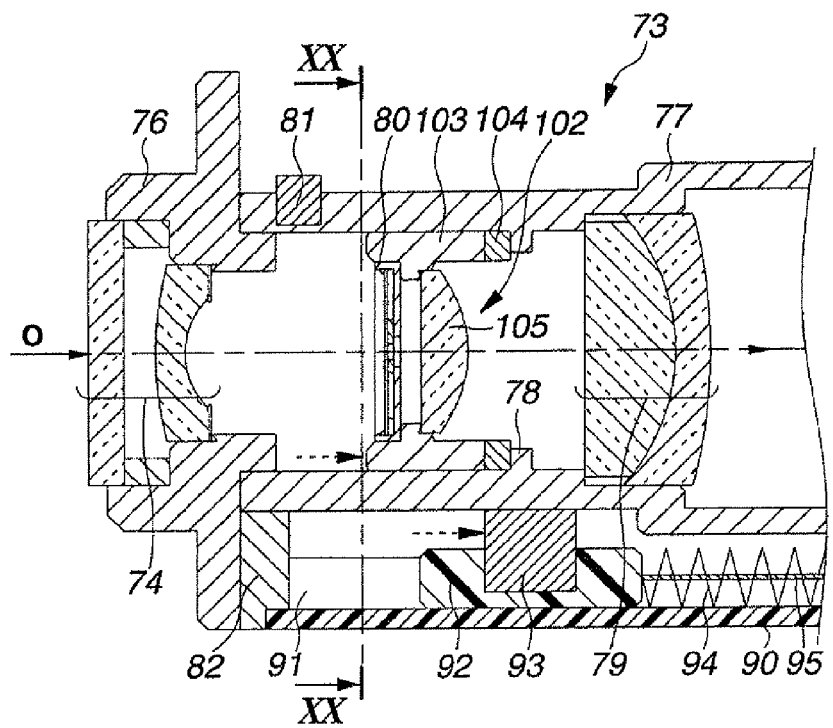
FIG. 19 is a sectional view showing a state in which a moving lens unit is positioned rearward.
Figure 20:
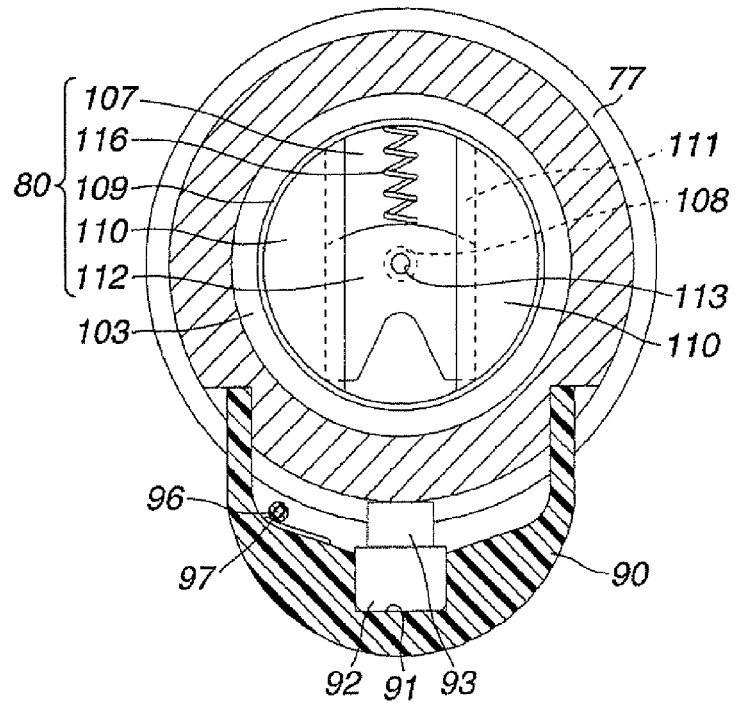
FIG. 20 is a sectional view taken along line XX-XX in FIG. 19.
Figure 21:
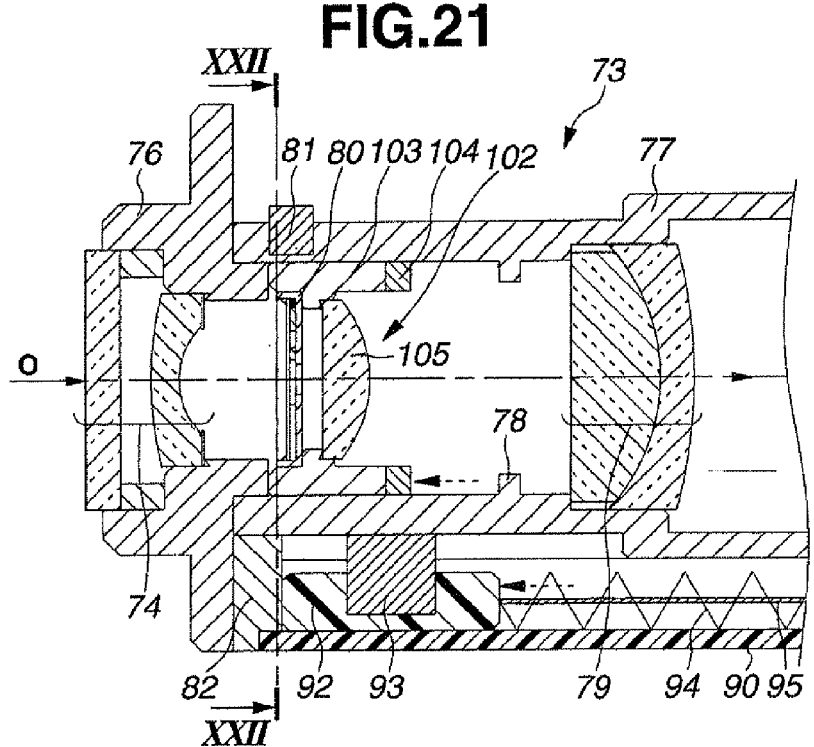
FIG. 21 is a sectional view showing a state in which the moving lens unit is positioned forward.
Figure 22:
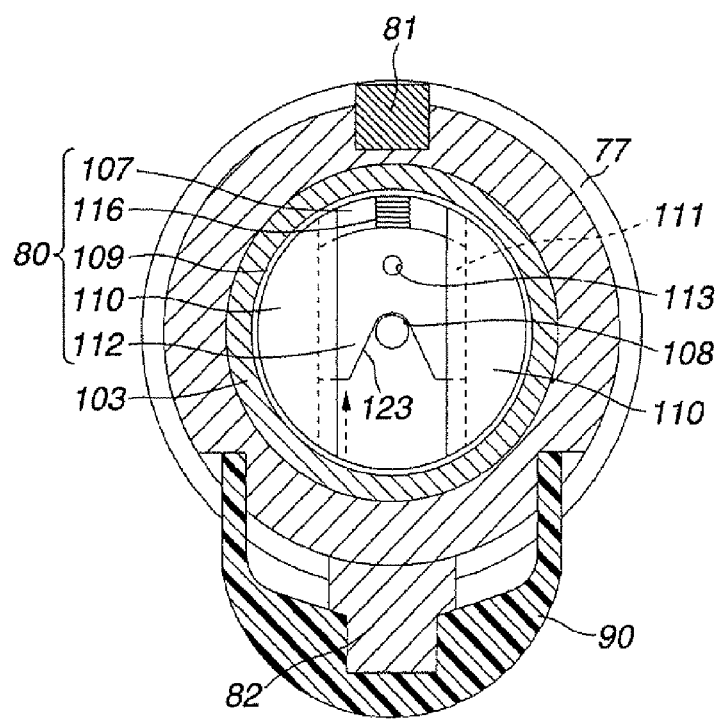
FIG. 22 is a sectional view taken along line XXII-XXII in FIG. 21.

FIGS. 13 to 22 relate to the fourth embodiment of the present invention; FIG. 13 is a diagram showing the configuration of a rigid electronic endoscope; FIG. 14 is a sectional view of an image pickup apparatus disposed in a distal end portion of the rigid electronic endoscope; FIG. 15 is a sectional view taken along line XV-XV in FIG. 14; FIG. 16 is an exploded perspective view of a diaphragm unit; FIG. 17 is a front view of the diaphragm unit; FIG. 18 is a sectional view taken along line XVIII-XVIII in FIG. 17; FIG. 19 is a sectional view showing a state in which a moving lens unit is positioned rearward; FIG. 20 is a sectional view taken along line XX-XX in FIG. 19; FIG. 21 is a sectional view showing a state in which the moving lens unit is positioned forward; and FIG. 22 is a sectional view taken along line XXII-XXII in FIG. 21.

As shown in FIG. 13, a rigid electronic endoscope 60 (hereinafter referred to simply as "endoscope") is configured mainly of an insertion portion 61, an operation portion 62 provided continuously with a proximal end of the insertion portion 61, a universal cord 63 extending from the operation portion 62, a scope connector 64 provided on a proximal end of the universal cord 63, and an electric connector 65 provided on an end portion of a cable extending from a side portion of the scope connector 64.

The insertion portion 61 of the endoscope 60 is configured of, in order from a distal end, a distal end portion 66, a bending portion 67 provided continuously with the distal end portion 66, a rigid tube portion 68 provided between the bending portion 67 and an operation portion 62. The rigid tube portion 68 in the present embodiment is formed of a nonflexible rigid tube formed from stainless steel or the like. An image pickup apparatus having an image pickup optical system described below is incorporated in the distal end portion 66.

The operation portion 62 of the endoscope 60 in the present embodiment is provided with two bending operation levers 69 and 70 operated by turning operations to perform an operation to bend the bending portion 67, and switches 71 for performing various operations. These bending operation levers 69 and 70 are operated in a turning manner to bend the bending portion 67 of the insertion portion 61 in four or two directions. The plurality of switches 71 provided on the operation portion 62 are operated when predetermined endoscopic functions, e.g., operations on the image pickup apparatus disposed in the distal end portion 66 are executed.

The endoscope 60 in the present embodiment has the scope connector 64 connected to a light source unit incorporating an illumination means such as a halogen lamp, and has the electric connector 65 connected to a video processor, although these connections are not shown in the figure.

Illumination light from the light source unit is transmitted through a light guide bundle passed from the universal cord 63 to the distal end portion 66 to be radiated from the distal end portion 66 to a subject. The video processor is connected to a monitor and outputs an endoscopic image picked up with the endoscope 60 to the monitor to display the image.

The image pickup apparatus in the present embodiment, disposed in the distal end portion 66 of the endoscope 60, will be described in more detail with reference to FIGS. 14 and 15.

As shown in FIG. 14, the image pickup apparatus 72 in the present embodiment is configured mainly of a lens unit 73, an image pickup element unit 83 fitted to the lens unit 73 at the rear of the same, and a movable lens drive mechanism 89 disposed along portions of outer peripheries of the lens unit 73 and the image pickup element unit 83.

The lens unit 73 is configured of a front lens group 74 constituting a front objective optical system including an observation lens disposed at a distal end surface of the distal end portion 66, a fixed front lens group frame 76 which is a fixed lens frame holding the front lens group 74 and formed of a nonmagnetic material, a fixed rear lens group frame 77 which is a fixed lens frame provided fittingly and continuously with a rear end portion of the fixed front lens group frame 76, holding a rear lens group 79 constituting a rear objective optical system, and formed of a nonmagnetic material in substantially cylindrical form, and a movable lens unit 102 disposed in the fixed rear lens group frame 77 so as to be able to move forward and rearward, and having a diaphragm unit 80 fitted and fixed in a distal end portion thereof.

The fixed rear lens group frame 77 has a permanent magnet (hereinafter referred to simply as "magnet") 81 fitted in an outer peripheral portion on the distal end side. A permanent magnet is used as the magnet 81 in the present embodiment. The magnet 81 is disposed at the upper side of the fixed rear lens group frame 77 as viewed toward the paper surface in FIG. 14.

The movable lens unit 102 is configured of a movable lens frame 103 formed of a nonmagnetic material, a magnetic member 104 fitted to a proximal end of the movable lens frame 103 and formed of a magnetic material in ring form, and a movable lens 105 held in the movable lens frame 103. The movable lens unit 102 is guided so as to be able to move straight forward or rearward along a shooting optical axis O in the movable lens frame 103.

The image pickup element unit 83 is configured mainly of a holding frame 84 holding an optical component 85 such as a cover glass, a solid-state image pickup element 86 which is an image sensor such as a CCD or a CMOS bonded to the optical component 85 so that its light receiving portion is surface-joined thereto, and a flexible printed circuit (FPC) 75 in which electronic component parts electrically connected to the solid-state image pickup element 86 are mounted and to which a plurality of communication lines 87 are electrically connected by soldering.

A distal end portion of the holding frame 84 is fitted and fixed in the fixed rear lens group frame 77 of the lens unit 73, and a heat-shrinkable tube 88 for covering and protecting the solid-state image pickup element 86 and other components is provided on a proximal end outer peripheral portion of the holding frame 84. The space in the heat-shrinkable tube 88 is filled with a protective adhesive so as to cover the solid-state image pickup element 86, the FPC 75 and the communication lines 87.

The movable lens drive mechanism 89 is configured of a frame 90 in which a guide groove 91 which is a recessed groove parallel to the shooting optical axis O is formed and having a concave shape is formed, a magnet hold base 92 guided and moved rectilinearly in the guide groove 91 and formed of a nonmagnetic material, a movable magnet 93 which is a permanent magnet fitted in an upper portion of the magnet hold base 92, a spring 94 which urges the magnet hold base 92 forward, a shape memory alloy (SMA) wire 95 joined to a proximal end portion of the magnet hold base 92, a pipe 98 made of a metal, e.g., stainless steel and fitted to a proximal end of the frame 90, an insulating tube 99, through which the SMA wire 95 in inserted, such as a PEEK tube having an insulating property and inserted in the pipe 98, a swaged electrode fitting 100 which is provided on a proximal end of the insulating tube 99, and to which the SMA wire 95 is joined, a power supply cable 101 electrically connected to the waged electrode fitting 100, and an insulating sheath 106 which covers a distal end portion of the insulating tube 99 and the swaged electrode fitting 100 as well as the power supply cable 101. The SMA wire 95 is connected to a proximal end portion of the magnet hold base 92 and thereafter bent back to be extended rearward as a ground (GND) wire 96 described below.

As shown in FIG. 15, the frame 90 is substantially U-shaped in section and has its upper end portions fitted to the fixed rear lens group frame 77 of the lens unit 73. In this fitted state, a space surrounded by an outside shape surface of the fixed rear lens group frame 77 and an inside shape surface of the frame 90 is formed. In this space, the magnet hold base 92 is guided by the guide groove 91 to move straight forward or rearward in a direction parallel to the shooting optical axis O together with the movable magnet 93.

For this forward/rearward movement of the magnet hold base 92, electric power is supplied from the power supply cable 101 to the SMA wire 95 connected to the rear end portion of the magnet hold base 92 via the swaged electrode fitting 100 to cause the SMA wire 95 itself to produce heat, contract and pull the magnet hold base 92 rearward against the forward urging force of the spring 94. The magnet hold base 92 is thus enabled to move rearward.

When the supply of electric power to the SMA wire 95 is stopped, the SMA wire 95 is returned to ordinary temperature to enable the magnet hold base 92 to move forward by receiving the forward urging force of the spring 94. After the magnet hold base 92 has been enabled to move forward, the distal end surface thereof is brought into abutment on an abutment member 82 fitted in a distal end of the frame 90 to limit the forward movability.

The SMA wire 95 is turned back at the magnet hold base 92 and electrically connected to the ground (GND) wire 96 (see FIG. 15) extending rearward and covered with an insulating tube 97.

The magnet hold base 92 is thus moved forward or rearward in the direction parallel to the shooting optical axis O together with the movable magnet 93. When the magnet hold base 92 moves in this way, the magnetic member 104 provided on the proximal end portion of the movable lens frame 103 is attracted by receiving magnetic force from the movable magnet 93 from the outside of the fixed rear lens group frame 77 to move forward or rearward in the direction parallel to the shooting optical axis O in the fixed rear lens group frame 77 together with the movable lens frame 103 by being interlocked with the forward/rearward movement of the movable magnet 93.

In other words, the movable lens unit 102 moves forward or rearward in the fixed rear lens group frame 77 by receiving magnetic action from the movable magnet 93 through the magnetic member 104 on the movable lens frame 103 holding the movable lens 105.

The distance through which the movable lens unit 102 moves forward or rearward is according to the focal distance corresponding to a predetermined zoom/telephoto state of the image pickup apparatus 72 variable with the movability of the movable lens 105 along the shooting optical axis O.

With respect to the rearward movability of the movable lens unit 102, a limiting projection 78 which projects inwardly in a diametric direction and which limits the movable position by abutting on a proximal end surface of the magnetic member 104 provided on the proximal end of the movable lens frame 103 is formed on an inner peripheral surface of the fixed rear lens group frame 77. With respect to the forward movability of the movable lens unit 102, a distal end surface of the movable lens frame 103 is brought into abutment on a proximal end surface of the fixed front lens group frame 76 to limit the movement.

That is, the movable range of the movable lens unit 102 along the shooting optical axis is defined between the position at which the movable lens frame 103 abuts on the fixed front lens group frame 76 and the position at which the magnetic member 104 abuts on the limiting projection 78 of the fixed rear lens group frame 77.

Further, the movable lens unit 102 moves forward or rearward in an enclosed space in the fixed rear lens group frame 77 closed in a sealing manner at the distal end with the front lens group 74 and the fixed front lens group frame 76 and closed with the rear lens group 79. That is, the image pickup apparatus 72 in the present embodiment is configured to move forward or rearward the movable lens unit 102 in the enclosed space in the fixed rear lens group frame 77 by the movable lens drive mechanism 89, thus being configured to have good moisture resistance.

The image pickup apparatus 72 in the present embodiment is also configured to enable selection between two states: a wide-angle state in which the movable lens unit 102 is positioned forward, and a telephoto state in which the movable lens unit 102 is positioned rearward, and the opening diameter $\phi$ of the diaphragm unit 80 optimizing the quality of light is variable according to the focal distances corresponding to these states.

The diaphragm unit 80 of the present embodiment in which the opening diameter $\phi$ is variable will be described in detail with reference to FIGS. 16 to 18.

As shown in FIG. 16, the diaphragm unit 80 is configured of a fixed diaphragm plate 107 having a diaphragm hole 108 at its center and formed of a nonmagnetic material in disk form, a diaphragm frame 109 formed of a nonmagnetic member in annular form, two retaining plates 110 formed of a nonmagnetic member in substantially semicircular form constituting a diaphragm blade retainer, a movable diaphragm blade 112 having a diaphragm hole 113 in its upper portion, having a cut 123 in its lower portion and formed of a magnetic material, and a spring 116 which is an urging member having one end portion fixed to an upper end portion of the movable diaphragm blade 112.

In the fixed diaphragm plate 107, an opening diameter $\phi$A of the diaphragm hole 108 (see FIG. 18) for adjusting the amount of shooting light in the optical system of the present embodiment by allowing only part of the shooting light to pass through the formed diaphragm hole 108 to satisfy a predetermined optical performance requirement is set. PTFE surface working or the like for reducing sliding frictional resistance to the movable diaphragm blade 112 is performed on the fixed diaphragm plate 107.

The outer peripheral surface of the diaphragm member 109 substantially coincides with the outside shape of the fixed diaphragm plate 107 and has a predetermined thickness larger than those of the movable diaphragm blade 112 and the retaining plates 110.

The two retaining plates 110 are disposed by being opposed to each other and have guide grooves 111 formed in edge portions on one side thereof facing each other when the retaining plates 110 are opposed to each other, as also described below. The guide grooves 111 guide the movable diaphragm blade 112 for vertical rectilinear movement by surface-contacting and slidably retaining opposite end portions of the movable diaphragm blade 112, while the movable diaphragm blade 112 is in contact with the fixed diaphragm plate 107. PTFE surface working or the like for reducing sliding frictional resistance to the movable diaphragm blade 112 is also performed on surfaces in the guide grooves 111.

PTFE surface working or the like for reducing sliding frictional resistance is performed on the movable diaphragm blade 112. In the diaphragm hole 113 formed in the movable diaphragm blade 112, an opening diameter 4B (see FIG. 18) for adjusting the amount of shooting light in the optical system of the present embodiment by allowing only part of the shooting light to pass to satisfy a predetermined optical performance requirement, smaller than the opening diameter $\phi$A of the diaphragm hole 108, is set.

In the movable diaphragm blade 112, the cut 123 extending on the side of a lower portion opposite from the upper portion on which the spring 116 is provided and having an upper portion cut into a circular-arc shape is formed. The cut 123 is formed so as to be larger than the diaphragm hole 108 of the fixed diaphragm plate 107.

The diaphragm frame 109 is fixed to a circumferential portion of one surface of the fixed diaphragm plate 107. The movable diaphragm blade 112 is disposed so as to surface-contact with the one surface of the fixed diaphragm plate 107 on which the diaphragm frame 109 is fixed.

Another end portion of the spring 116 opposite from the one end portion fixed to the movable diaphragm blade 112 is fixed to an inner surface of the diaphragm frame 109 by bonding with an adhesive or the like. The movable diaphragm blade 112 has its two side portions brought into engagement with the guide grooves 111 of the retaining plate 110 by the two retaining plates 110 and is vertically slidably interposed between the fixed diaphragm plate 107 and the two retaining plates 110 while being pressed against the fixed diaphragm plate 107. The two retaining plates 110 are fixed to the diaphragm frame 109 in a state of being spaced apart from each other by such a distance as not to close the diaphragm holes 108 and 113.

The diaphragm unit 80 of the present embodiment thus assembled is fitted and fixed in a distal end portion of the movable lens frame 103 of the movable lens unit 102, as shown in FIG. 2, while positioning the movable diaphragm blade 112 on the front side, as shown in FIGS. 17 and 18.

Detailed description will be made below, with reference to FIGS. 19 to 22, of an action to vertically move the movable diagram blade 112 in the diaphragm unit 80 interlocked with the forward/rearward movement of the movable lens unit 102 along the shooting optical axis O in the image pickup apparatus 72 of the present embodiment thus configured.

To establish a telephoto state by rearward positioning, as shown in FIGS. 19 and 20, in the image pickup apparatus 72 in the present embodiment, a current is applied to the SMA wire 95 to cause the SMA wire 95 to contract, as described above. The magnet hold base 92 on which the movable magnet 93 is provided is thereby pulled rearward against the forward urging force of the spring 94.

Then, the magnetic member 104 of the movable lens unit 102 is attracted to the movable magnet 93 by magnetic action and is moved rearward in the fixed rear lens group frame 77 by being interlocked with the movable magnet 93, and the proximal end surface of the magnetic member 104 is brought into abutment on the limiting projection 78 of the fixed rear lens group frame 77 to limit the rearward movement. The movable lens unit 102 is thereby stopped at the telephoto position corresponding to the predetermined set focal distance.

At this time, a downward urging force of the movable magnet 93 side is applied to the movable diaphragm blade 112 of the diaphragm unit 80 by the spring 116 on the upper portion side. As a result, the lower end portion of the movable diaphragm blade 112 is brought into abutment on the diaphragm frame 109. In this state, the diaphragm hole 113 of the movable diaphragm blade 112 is aligned with a center of the diaphragm hole 108 of the fixed diaphragm plate 107, and the movable diaphragm blade 112 is superposed so as to cover the periphery of the diaphragm hole 108. That is, at this time, the diaphragm unit 80 has the stop value for adjusting the amount of shooting light according to the opening diameter 4B of the diaphragm hole 113 of the movable diaphragm blade 112.

To establish a wide-angle state by forward positioning, in the present embodiment, as shown in FIGS. 21 and 22, in the image pickup apparatus 72 shown in FIG. 14, application of the current to the SMA wire 95 is stopped to restore the length of the SMA wire 95 at ordinary temperature. The magnet hold base 92 on which the movable magnet 93 is provided is moved by being pushed forward by the urging force of the spring 94.

At this time, by the magnetic member 104 receiving the magnetic action from the movable magnet 93, the movable lens unit 102 is moved forward in the fixed rear lens group frame 77 in a state of being interlocked with the movement of the movable magnet 93. The distal end surface of the movable lens frame 103 is then brought into abutment on the proximal end surface of the fixed front lens group frame 76 to limit the forward movement of the movable lens unit 102. The movable lens unit 102 is thereby stopped at the zooming position corresponding to the predetermined set focal distance.

At this time, the movable diaphragm blade 112 of the diaphragm unit 80 is moved upward by being attracted to the magnet 81 provided in the upper portion of the fixed rear lens group frame 77 against the downward urging force of the spring 116 on the upper portion side, as shown in FIG. 22. That is, when the diaphragm unit 80 is moved forward together with the movable lens unit 102, it is moved to a position close to the magnet 81 in the fixed rear lens group frame 77. Therefore the movable diaphragm blade 112 formed of a magnetic material receives the magnetic action of the magnet 81 to be attracted while being guided by the guide grooves 111 of the retaining plates 110 so as to be move rectilinearly.

In this state, the diaphragm hole 113 of the movable diaphragm blade 112 is moved to a position above the diaphragm hole 108 of the fixed diaphragm plate 107, and the diaphragm hole 108 is exposed through the cut 123. That is, at this time, the diaphragm unit 80 has the stop value for adjusting the amount of shooting light according to the opening diameter φA of the diaphragm hole 108 of the fixed diaphragm plate 107.

Thus, in the image pickup apparatus 72 of the present embodiment, the movable diaphragm blade 112 of the diaphragm unit 80 is moved vertically by being guided in rectilinear movement by the guide grooves 111 of the retaining plates 110 according to the forward/rearward movement of the movable lens unit 102 along the shooting optical axis O according to the two telephoto and wide-angle states.

That is, when the diaphragm unit 80 is moved forward together with the movable lens unit 102, the movable diaphragm blade 112 formed of a magnetic material is brought close to the magnet 81 and therefore receives magnetic force from the magnet 81 to be attracted to the magnet 81 by the force larger than the urging force of the spring 116. Meanwhile, when the diaphragm unit 80 is moved rearward together with the movable lens unit 102, the movable diaphragm blade 112 is moved away from the magnet 81 and the magnetic force from the magnet 81 is reduced. As a result, the urging force of the spring 116 prevails over the magnetic force and the movable diaphragm blade 112 moves downward.

The magnet 81 is disposed at a position shifted further forward in the front-rear-direction along the shooting optical axis, i.e., in the front-rear direction along the major axis of the image pickup apparatus 72, relative to the position to which the movable magnet 93 is moved forward to reach the wide-angle position, and opposite from the movable magnet 93 with respect the shooting optical axis O. In the present embodiment, the positions in which the magnets 81 and 93 are disposed, the magnetic forces of the magnets 81 and 93 acting on the movable diaphragm blade 112 and the urging force of the spring 116 are set so that even when the movable diaphragm blade 112 formed of a magnetic material receives the urging force of the spring 116 and magnetic force from the movable magnet 93 at the position reached by forward movement to establish the wide-angle state, the movable diaphragm blade 112 can be sufficiently moved upward by the magnetic force of the magnet 81. Also, the position in which the magnet 81 is disposed, the magnetic force of the magnet 81 acting on the movable diaphragm blade 112 and the urging force of the spring 116 are set so that even when the movable diaphragm blade 112 formed of a magnetic material receives magnetic force from the movable magnet 81 at the position reached by rearward movement to establish the telephoto state, the movable diaphragm blade 112 can be sufficiently moved downward by the urging force of the spring 116.

As described above, the image pickup apparatus 72 provided with the zooming function according to the present embodiment is arranged to move the movable lens unit 102 forward and rearward along the shooting optical axis O in the enclosed space by the magnetic action of the movable lens drive mechanism 89, thereby has a structure with good moisture resistance, and can also have a simple structure in which the diaphragm is opened and closed by the magnetic action of the diaphragm unit 80 capable of changing the amount of shooting light according to a telephoto state or a wide-angle state. In particular, the image pickup apparatus 72 of the present embodiment is smaller in size but has advantageously improved assembly facility because the structure for changing the diaphragm by the diaphragm unit 80 is simple.

Needless to say, the above-described configuration may be provided in the image pickup apparatuses described above in the descriptions of the first to third embodiments.

(Fifth Embodiment)

A fifth embodiment of the present invention will be described below with reference to FIGS. 23 to 27.

Figure 23:
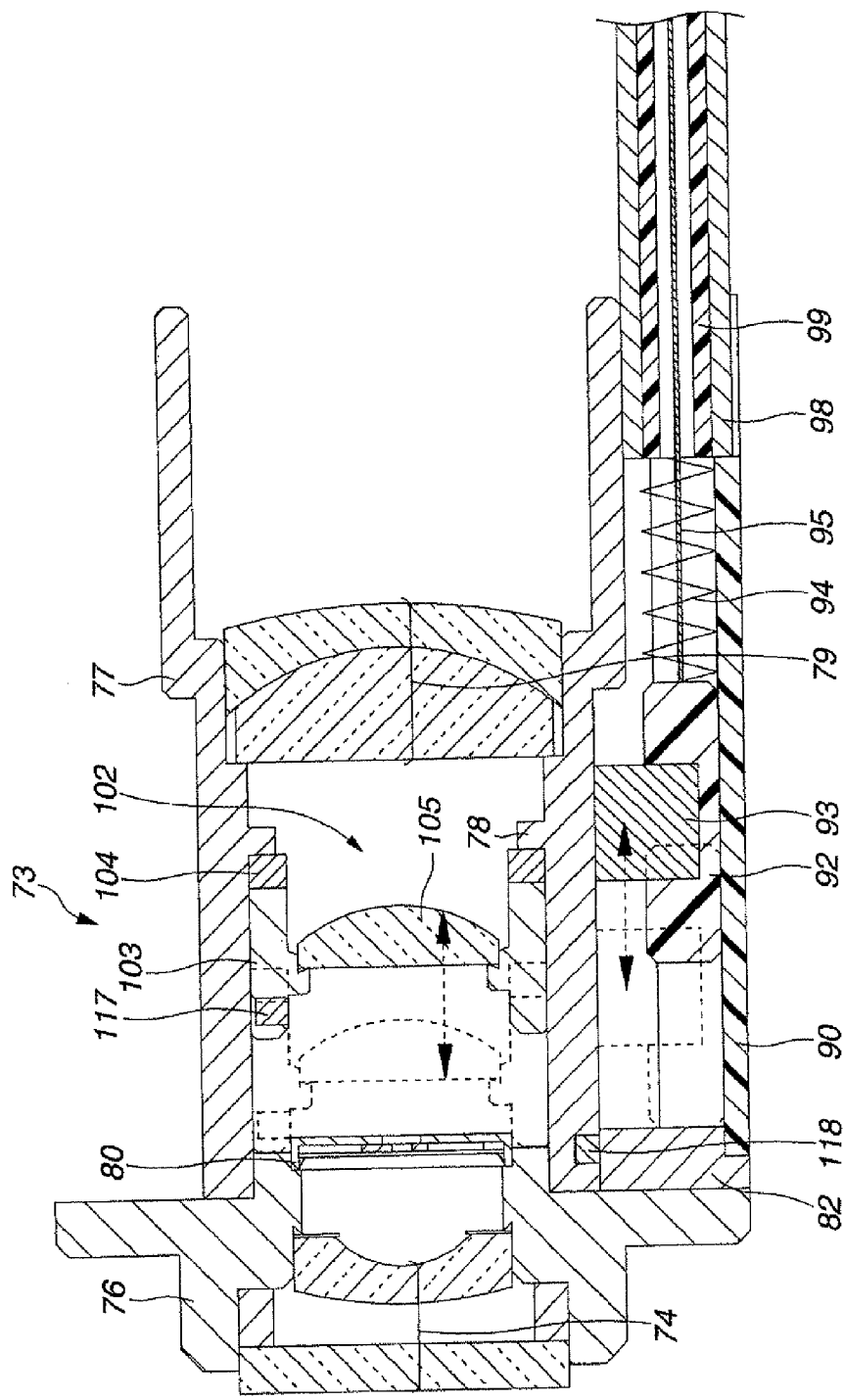
FIG. 23 is a partial sectional view showing a configuration of an image pickup apparatus according to a fifth embodiment.
Figure 24:
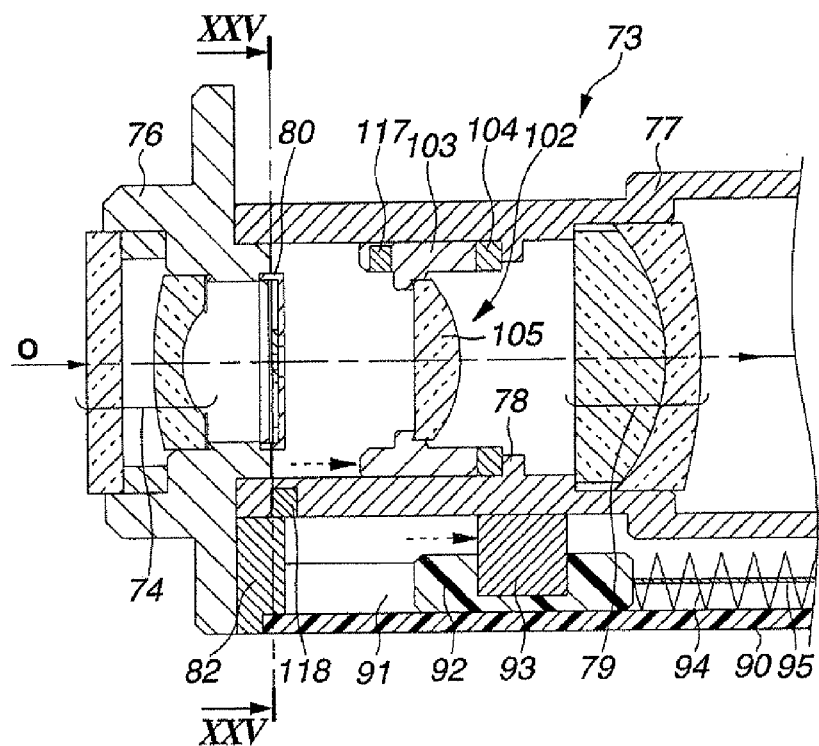
FIG. 24 is a sectional view showing a state in which a movable lens unit is positioned rearward.
Figure 25:
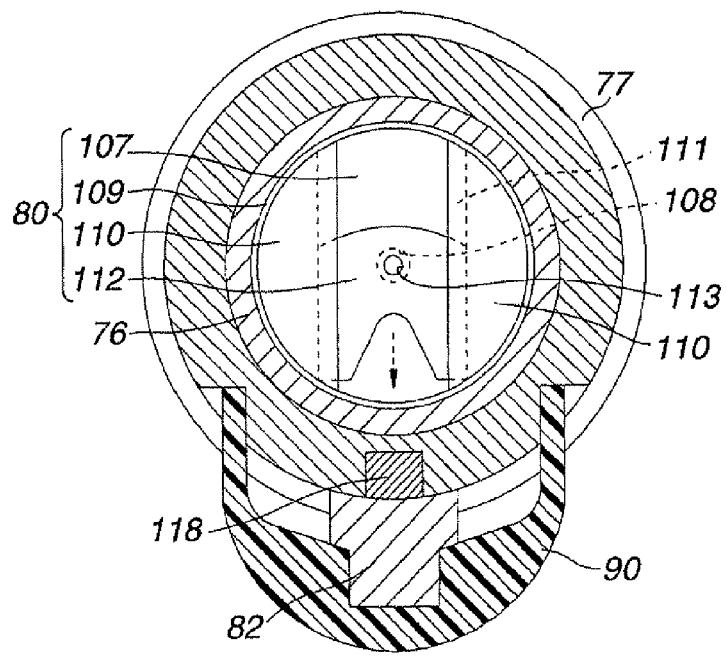
FIG. 25 is a sectional view taken along line XXV-XXV in FIG. 24.
Figure 26:
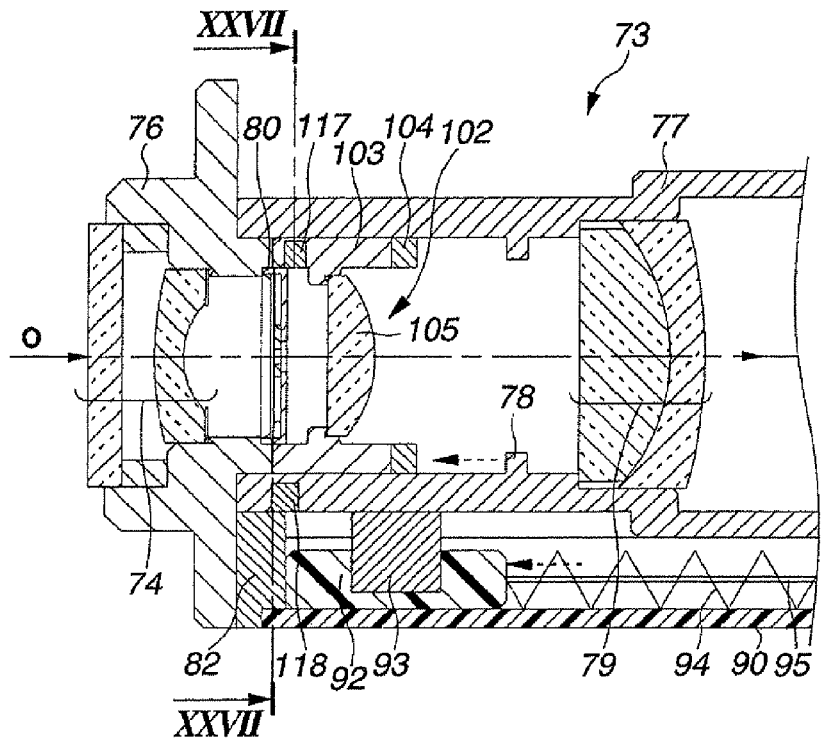
FIG. 26 is a sectional view showing a state in which the movable lens unit is positioned forward.
Figure 27:
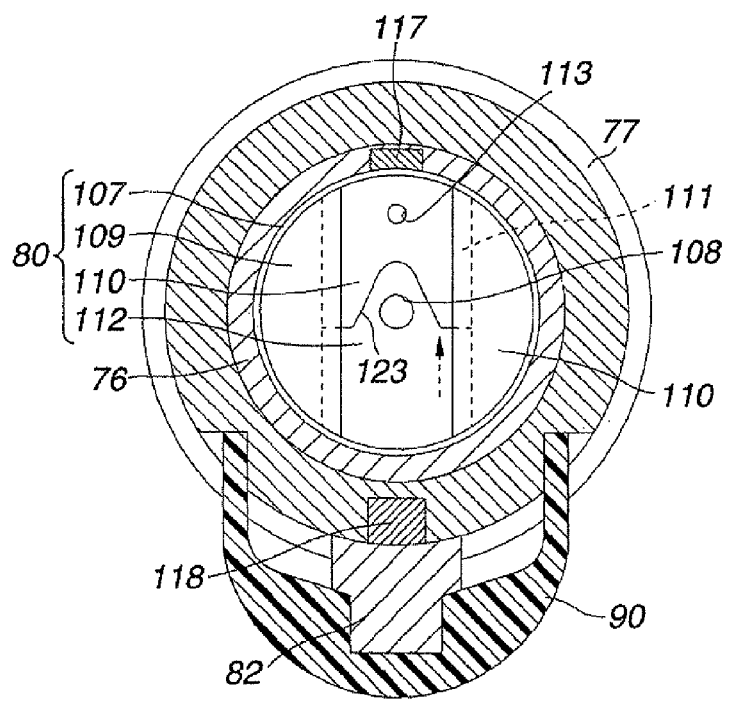
FIG. 27 is a sectional view taken along line XXVII-XXVII in FIG. 26.

FIGS. 23 to 27 relate to the fifth embodiment of the present invention; FIG. 23 is a partial sectional view showing a configuration for an image pickup apparatus;

FIG. 24 is a sectional view showing a state in which a movable lens unit is positioned rearward; FIG. 25 is a sectional view taken along line XXV-XXV in FIG. 24; FIG. 26 is a sectional view showing a state in which the movable lens unit is positioned forward; and FIG. 27 is a sectional view taken along line XXVII-XXVII in FIG. 26. In the following description, the same components in the configuration as those in the above-described fourth embodiment are indicated by the same reference numerals, and the detailed description thereof will not be repeated.

In the image pickup apparatus 72 of the present embodiment, the diaphragm unit 80 is fitted and fixed to a proximal end portion of the fixed front lens group frame 76. Also, a magnet 117 is fittingly disposed in an upper portion in a distal end portion of the movable lens frame 103 of the movable lens unit 102. Further, in the fixed rear lens group frame 77, a magnet 118 is fittingly disposed at a distal-end lower outer peripheral position immediately below the diaphragm unit 80.

That is, the image pickup apparatus 72 of the present embodiment is configured by disposing on the fixed front lens group frame 76 the diaphragm unit 80 fixed in the movable lens unit 102 in the fourth embodiment.

Also in the thus-configured image pickup apparatus 72 in the present embodiment, when a telephoto state is established by rearward positioning, as shown in FIG. 24, the movable diaphragm blade 112 of the diaphragm unit 80 receives the magnetic force of the magnet 118 provided immediately below the diaphragm unit 80 to be attracted to a lower position on the magnet 118 side, thereby bringing the lower end portion into abutment on the diaphragm frame 109 as shown in FIG. 25. In this state, the diaphragm hole 113 of the movable diaphragm blade 112 is aligned with a center of the diaphragm hole 108 of the fixed diaphragm plate 107, and the movable diaphragm blade 112 is superposed so as to cover the periphery of the diaphragm hole 108. That is, at this time, the diaphragm unit 80 has the stop value for adjusting the amount of shooting light according to the opening diameter 4B of the diaphragm hole 113 of the movable diaphragm blade 112.

Meanwhile, also in the image pickup apparatus 72 in the present embodiment, when a wide-angle state is established by forward positioning, as shown in FIG. 26, the movable diaphragm blade 112 of the diaphragm unit 80 receives the magnetic force of the magnet 117 provided in a distal end upper portion of the movable lens frame 103 and is attracted by this force to move upward against a downward attraction force based on the magnetic force of the magnet 118 existing immediately below, as shown in FIG. 27. That is, when the movable lens unit 102 is moved forward, the magnet 117 in the movable lens frame 103 is moved to a position close to an upper portion of the diaphragm unit 80 and, therefore, the movable diaphragm blade 112 formed of a magnetic material receives the magnetic action of the magnet 117 to be attracted upward while being guided by the guide grooves 111 of the retaining plates 110 so as to be move rectilinearly.

In this state, the diaphragm hole 113 of the movable diaphragm blade 112 is moved to a position above the diaphragm hole 108 of the fixed diaphragm plate 107, and the diaphragm hole 108 is exposed through the cut 123. That is, at this time, the diaphragm unit 80 has the stop value for adjusting the amount of shooting light according to the opening diameter φA of the diaphragm hole 108 of the fixed diaphragm plate 107.

That is, when the movable lens unit 102 is moved forward, the magnet 117 is moved closer to the movable diaphragm blade 112 formed of a magnetic material and the movable diaphragm blade 112 receives the magnetic force of the magnet 117 and moves upward by being attracted by the magnetic force larger than the magnetic force of the magnet 118. Meanwhile, when the movable lens unit 102 is moved rearward, the magnet 117 is moved away from the movable diaphragm blade 112 and the magnetic force from the magnet 117 is reduced. As a result, the magnetic force of the magnet 118 prevails over the magnetic force from the magnet 117 and the movable diaphragm blade 112 moves downward.

The magnetic force of the magnet 117 of the movable lens unit 102 is set to a value higher than that of the magnet 118 disposed in the fixed rear lens group frame 77 opposite from the magnet 117 with respect to the optical axis O when the movable lens unit 102 is moved forward, which value is high enough to attract the movable diaphragm blade 112 against the magnetic force of the magnet 118.

The diaphragm unit 80 of the present embodiment is configured to advance and retract the movable diaphragm blade 112 in a direction perpendicular to the shooting optical axis O by means of the two magnets 117 and 118 and, therefore, as shown in FIGS. 25 and 27, does not require the spring 116 provided in the fourth embodiment.

The image pickup apparatus 72 of the present embodiment can have the same advantages as those of the apparatus of the first embodiment and is free from the need for the provision of the spring 116 in the diaphragm unit 80. Therefore, only a relationship of magnetic force may be set between the two magnets 117 and 118 and the configuration is simplified.

Figure 28:
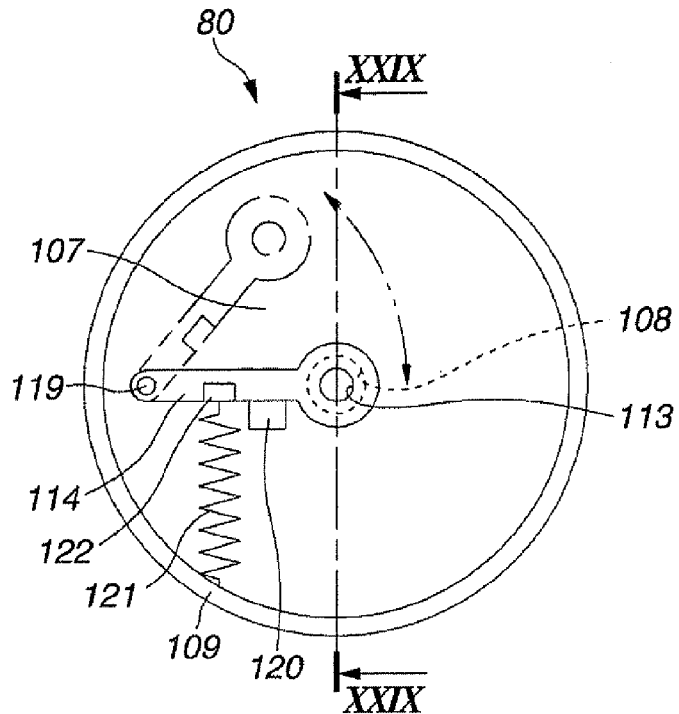
FIG. 28 is a front view of the configuration of a diaphragm unit according to a first modified example.
Figure 29:
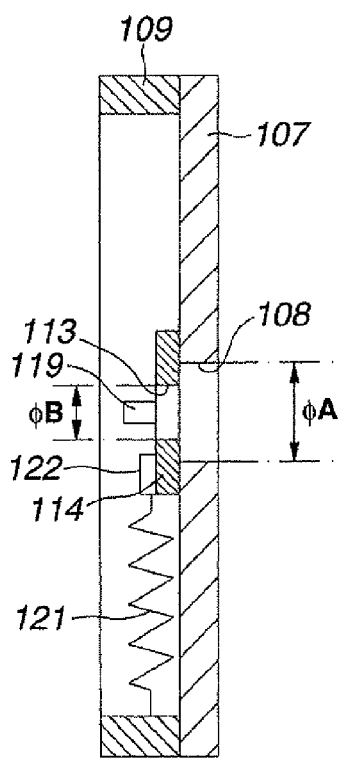
FIG. 29 is a sectional view taken along line XXIX-XXIX in FIG. 28.
Figure 30:
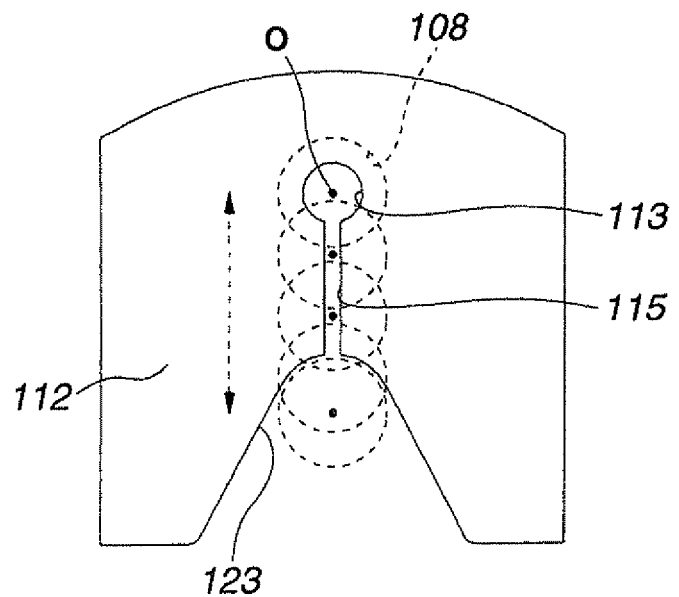
FIG. 30 is a front view of a configuration of a diaphragm blade according to a second modified example.
Figure 31:
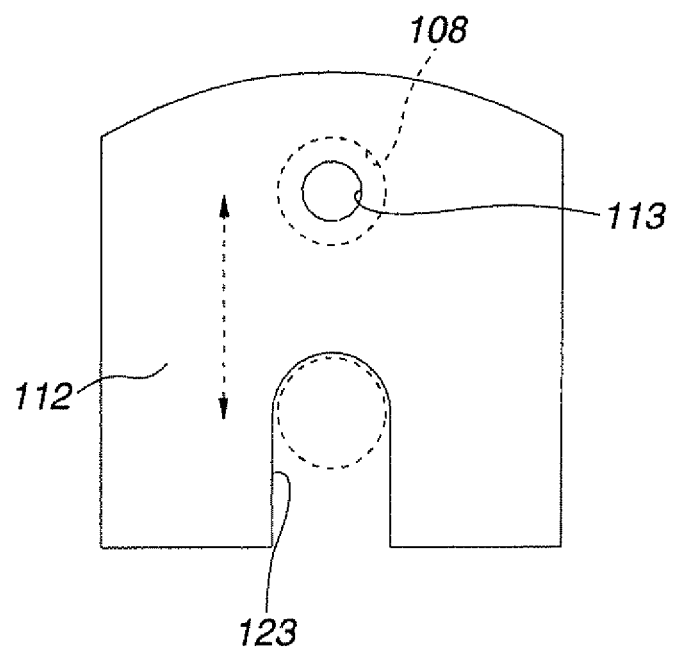
FIG. 31 is a front view of a configuration of a diaphragm blade according to a third modified example.

The diaphragm unit 80 described in each of the above-described embodiments is only an example. Configurations such as shown in FIGS. 28 to 31 may alternatively be adopted. FIG. 28 is a front view of a configuration of a diaphragm unit according to a first modified example; FIG. 29 is a sectional view taken along line XXIX-XXIX in FIG. 28; FIG. 30 is a front view of a configuration of a diaphragm blade according to a second modified example; and FIG. 31 is a front view of a configuration of a diaphragm blade according to a third modified example.

For example, as shown in FIGS. 28 and 29, the configuration of a movable diaphragm blade 114 in the diaphragm unit 80 differs from that in each embodiment. More specifically, the movable diagram blade 114 is formed of a magnetic material, and an extended end portion of an arm portion extending from a circular outer peripheral portion in which the diaphragm hole 113 is formed is turnably disposed on the fixed diaphragm plate 107 by means of a blade shaft 119.

A spring attachment member 122 is disposed on the arm portion of the movable diaphragm blade 114, and one end of a spring 121 is connected to the spring attachment member 122. The spring 121 urges the movable diaphragm blade 114 in such a manner that the movable diaphragm blade 114 is pulled downward. The other end of the spring 121 is fixed in an inner surface of the diaphragm frame 109.

On the fixed diaphragm plate 107, a blade stop member 120 to be brought into abutment on the movable diaphragm blade 114 urged by the spring 121 to limit the position of the movable diaphragm blade 114 at a position at which the diaphragm hole 113 of the movable diaphragm blade 114 is superposed on the diaphragm hole 108 is provided.

Also in the thus-configured diaphragm unit 80, the movable diaphragm blade 114 receives magnetic force from a magnet which is brought closer thereto with the advancing/retracting movement of the movable lens unit 102 or the forward movement in the telephoto state of the image pickup apparatus 72, as in each of the embodiments described above, and is thereby given a force for upward attraction to be turned upward on the blade shaft 119 against the urging fore of the tensile force of the spring 121.

Meanwhile, with the rearward movement of the movable lens unit 102 in the wide-angle state of the image pickup apparatus 72, the magnetic force from the magnet is reduced and the movable diaphragm blade 114 is turned by being pulled downward by the spring 121 to be brought into abutment on the blade stop member 120 and stopped at the position at which the diaphragm hole 113 is superposed on the diaphragm hole 108.

Thus, the diaphragm unit 80 constitutes a mechanism to change the opening diameter φ of the diaphragm. Also with the thus-configured diaphragm unit 80, the same advantages and effects as those in the above-described embodiments can also be obtained.

It is preferable to provide the movable diaphragm blade 112 with a slit 115 connecting the diaphragm hole 113 and the cut 123, as shown in FIG. 30. The slit 115 is formed at a position at which the shooting optical path O passes through the movable diaphragm blade 112 in advancing/retracting movement.

The slit 115 is provided in the movable diaphragm blade 112 in this way to avoid an instantaneous break of the shooting optical path O at the time of advancing/retracting movement of the movable diaphragm blade 112, thus preventing instantaneous disappearance of an image taken by the image pickup apparatus 72 at the time of telephoto/wide-angle switch. Also, the image pickup apparatus 72 is capable of preventing disappearance of a taken image even in a case where the movable diaphragm blade 112 stops halfway through the advancement or retraction stroke before correctly advancing or retracting due to some fault.

Further, the cut 123 formed in the movable diaphragm blade 112 may only enable the diaphragm hole 108 of the fixed diaphragm plate 107 to be completely exposed when the movable diaphragm blade 112 is moved upward. Therefore, the cut 123 may be formed into any shape, e.g., a shape having a semicircular upper portion and vertically extending lower portions, as shown in FIG. 31.

In each of the above-described embodiments, a permanent magnet is used as the magnet for magnetically moving the movable diaphragm blade 112 for the purpose of simplifying the configuration. However, the present invention is not limited thereto. An electromagnet or the like may alternatively be used.

Further, while the movable diaphragm blade 112 is formed as a magnetic member, the movable diaphragm blade 112 itself may be a magnet. In such a case, the polarities of the magnets may be set with respect to attraction and repellency between the magnets according to the movable directions.

The invention described by referring to the embodiments is not limited to the embodiments and the modified examples. Various changes and modifications may be made in the embodiments and modified examples in an implementation stage without departing from the gist of the invention. Further, the above-described embodiments include variations of the invention in various stages, which can be extracted according to suitable combinations of the plurality of constituent features disclosed.

For example, if the problems to be solved by the invention can be solved and the described effects can be obtained even in a case where several ones of all the constituent features described in the embodiments are deleted, a configuration as a result of deletion of the constituent features can be extracted as the invention.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. An image pickup apparatus comprising:
   a movable lens unit having a movable lens frame holding a movable lens;
   a fixed lens frame in which a plurality of objective optical systems are disposed, and in which the movable lens unit is held so as to be able to advance and retract in a shooting optical axis direction;
   a diaphragm unit which has a diaphragm blade formed of a magnetic material and movable in a first direction and a second direction opposite to the first direction, and adjusts an amount of shooting light by moving the diaphragm blade;
   a first urging member provided at the movable lens unit and including a first magnet which urges the diaphragm blade in the first direction by a first magnetic force as a first urging force according to the advancement and retraction of the movable lens unit; and
   a second urging member which urges the diaphragm blade in the second direction by a second urging force smaller than the first urging force,
   wherein, according to the advancement and retraction of the movable lens unit, when the first urging member moves close to the diaphragm blade, the diaphragm blade moves in the first direction by receiving the first urging force against the second urging force, and when the first urging member moves away from the diaphragm blade, the diaphragm blade moves in the second direction by receiving the second urging force.

2. The image pickup apparatus according to claim 1, wherein the movable lens unit has a magnetic member, and the image pickup apparatus further comprises a movable lens drive mechanism which advances and retracts the magnetic member of the movable lens unit by magnetic force from outside of the fixed lens frame.

3. The image pickup apparatus according to claim 2, wherein the movable lens drive mechanism is an actuator comprising:
   a moving magnet which attracts the magnetic member of the movable lens unit;

a shape memory alloy wire which contracts and pulls the moving magnet rearward when supplied with electric power; and a third urging member which urges the moving magnet forward.

4. The image pickup apparatus according to claim 1, wherein the diaphragm unit is disposed in the fixed lens frame.

5. The image pickup apparatus according to claim 1, wherein each of the movable lens frame and the fixed lens frame is formed of a nonmagnetic material.

6. The image pickup apparatus according to claim 1, wherein the fixed lens frame has an enclosed space closed in a sealing manner at front and rear positions by the plurality of objective optical systems, and the movable lens unit is disposed in the enclosed space so as to be able to advance and retreat in the shooting optical axis direction.

7. The image pickup apparatus according to claim 1, wherein the second urging member includes a second magnet which generate a second magnetic force as the second urging force.

8. The image pickup apparatus according to claim 7, wherein the second urging member is disposed at the fixed lens frame.

\* \* \* \* \*